United States Patent
Takahashi et al.

(10) Patent No.: US 8,018,237 B2
(45) Date of Patent: Sep. 13, 2011

(54) BROKEN PIECE DETECTING SENSOR

(75) Inventors: Toru Takahashi, Iwata (JP); Tomomi Ishikawa, Iwata (JP)

(73) Assignee: NTN Corporation, Osaka (JP)

( * ) Notice: Subject to any disclaimer, the term of this patent is extended or adjusted under 35 U.S.C. 154(b) by 351 days.

(21) Appl. No.: 12/311,312

(22) PCT Filed: Sep. 5, 2007

(86) PCT No.: PCT/JP2007/000963
§ 371 (c)(1),
(2), (4) Date: Mar. 26, 2009

(87) PCT Pub. No.: WO2008/038407
PCT Pub. Date: Apr. 3, 2008

(65) Prior Publication Data
US 2009/0320567 A1 Dec. 31, 2009

(30) Foreign Application Priority Data

| Sep. 26, 2006 | (JP) | 2006-260531 |
| Sep. 26, 2006 | (JP) | 2006-260532 |
| Sep. 26, 2006 | (JP) | 2006-260533 |
| Oct. 24, 2006 | (JP) | 2006-288754 |
| Oct. 24, 2006 | (JP) | 2006-288757 |

(51) Int. Cl.
*G01R 27/26* (2006.01)
*G01R 33/12* (2006.01)
(52) U.S. Cl. .......... 324/661; 324/204
(58) Field of Classification Search .......... None
See application file for complete search history.

(56) References Cited

U.S. PATENT DOCUMENTS

| 4,219,805 A | 8/1980 | Magee et al. |
| 4,513,613 A | 4/1985 | Darves-Bornoz et al. |
| 4,731,578 A | 3/1988 | Tsaprazis |
| 5,315,243 A * | 5/1994 | Kempster et al. ............ 324/204 |
| 5,388,448 A | 2/1995 | Showalter et al. |
| 5,528,138 A * | 6/1996 | Rumberger et al. ......... 324/204 |
| 5,663,642 A * | 9/1997 | Rumberger et al. ......... 324/204 |
| 5,811,664 A * | 9/1998 | Whittington et al. ........ 324/204 |
| 2005/0213088 A1 | 9/2005 | Brewer et al. |

(Continued)

FOREIGN PATENT DOCUMENTS

JP 55-52943 4/1980

(Continued)

OTHER PUBLICATIONS

*International Search Report for International Application* No. PCT/JP2007/000963, mailed Oct. 30, 2007.

(Continued)

*Primary Examiner* — Jermele M Hollington

(57) ABSTRACT

To provide a broken piece detecting sensor assembly capable of stably detecting broken piece admixed in a fluid, which broken piece is made of material characterized by non-metal, non-magnetic and non-electroconductive characteristics such as ceramics. This broken piece detecting sensor assembly is a sensor for detecting broken piece admixed in a fluid. Provided are two opposed flat plates, a shift mechanism for moving at least one of the two flat plates in a confronting direction to allow the broken piece to be sandwiched between those two flat plates, and measuring and determining section. The measuring and determining section is operable to measure the distance between the two flat plates to thereby detect the presence or absence of the broken piece, the size of the broken piece or the amount of the broken piece accumulated.

12 Claims, 28 Drawing Sheets

U.S. PATENT DOCUMENTS

2006/0196254 A1* 9/2006 Fjerdingstad et al. ....... 73/64.56
2009/0007700 A1* 1/2009 Fjerdingstad et al. ..... 73/863.71

FOREIGN PATENT DOCUMENTS

| JP | 58-218602 | 12/1983 |
| JP | 60-3576 | 1/1985 |
| JP | 61-253455 | 11/1986 |
| JP | 2703502 | 10/1997 |
| JP | 2865857 | 12/1998 |
| JP | 2000-321248 | 11/2000 |
| JP | 2005-274575 | 10/2005 |
| WO | 90/07705 | 7/1990 |

OTHER PUBLICATIONS

English Translation of the International Preliminary Report of Patentability mailed Apr. 9, 2009 and issued in corresponding International Patent Application PCT/JP2007/000963.

* cited by examiner

BROKEN PIECE DETECTING SENSOR

CROSS REFERENCE TO RELATED APPLICATIONS

This application claims the benefit under 35 U.S.C. §371, of PCT International Application No. PCT/JP2007/000963, filed Sep. 5, 2007, which claimed priority to the following:

Japanese Application No. 2006-260531, filed Sep. 26, 2006;

Japanese Application No. 2006-260532, filed Sep. 26, 2006;

Japanese Application No. 2006-260533, filed Sep. 26, 2006;

Japanese Application No. 2006-288754, filed Oct. 24, 2006;

Japanese Application No. 2006-288757, filed Oct. 24, 2006; the disclosures of which are hereby incorporated by reference.

BACKGROUND OF THE INVENTION

1. Field of the Invention

The present invention relates to a broken piece detecting sensor assembly for detecting the presence of broken piece admixed into a liquid such as, for example, a lubricant oil.

2. Description of the Prior Art

Hitherto, as a device for detecting the admixture of metallic particles or powdery metal, resulting from frictional wear and/or breakage of, for example, a combustion engine, a transmission and/or bearing assemblies, into the lubricant oil used in automotive vehicles, aircrafts or helicopters, the metallic broken piece detecting device generally called as a metal check sensor, an oil check sensor or a broken piece sensor has been suggested. (See the Japanese Laid-open Patent Publications No. S55-052943, No. S61-253455 and No. 2000-321248, and the Japanese Patents No. 2703502 and No. 2865857.) Such metallic broken piece detecting device is utilized as a mean for inspecting the soundness of various equipments such as, for example, a combustion engine, a gear box and/or bearing assemblies and is capable of providing information concerning deterioration taking place at various sites of the device to be inspected before any destructive trouble occurs at such sites.

Particularly in aircraft jet engines, downsizing and increased speed orientation thereof are currently desired for. While a spindle bearing assembly hitherto employed in the aircraft jet engine makes use of bearing rolling elements made of a metallic material, the currently utilized material for the bearing rolling elements has now come to a deadlock in promoting the increased speed orientation. In order for the material for the bearing rolling element to accommodate the high speed orientation, it is necessary for the rolling elements of the bearing assembly to be made in the form of ceramic balls or ceramic rollers made of, for example, silicon nitride ($Si_3N_4$). Also, where the ceramic balls or the ceramic rollers are employed in the bearing assembly for the jet engine, the performance is likely to be increased considerably, accompanied by increase of the efficiency of the jet engine to such an extent that the environmental loading can be reduced. On the other hand, with the conventional metallic broken piece detecting device, only broken remains of metallic material, magnetic material or electroconductive material can be detected, but it is incapable of detecting broken remains of ceramic material that is characteristically non-metallic, non-magnetic and non-electric conductive. Accordingly, in the case of the bearing assembly in which the ceramics, for example, are employed as material for the bearing rolling elements, no information concerning deterioration taking place in the bearing rolling elements before occurrence of any destructive trouble can be made available from the metallic broken piece detecting device. For this reason, bearing assemblies of such a structure are currently utilized only in aircrafts having a limited application.

SUMMARY OF THE INVENTION

An object of the present invention is to provide a broken piece detecting sensor assembly capable of stably detecting the presence or absence of, the size of or the accumulated amount of, broken piece admixed in a fluid without being affected by the amount of broken piece admixed.

The broken piece detecting sensor assembly of the present invention is a sensor for detecting broken piece admixed in a fluid and includes two flat plates confronting each other, a shift mechanism for moving at least one of the flat plates in a confronting direction, and a measuring and determining section for measuring a distance between the flat plates to thereby detect a presence of the broken piece, a size of the broken piece or an amount of the broken piece accumulated. According to this construction, since one of the two flat plates is operated to allow the capacitance between those two flat plates to be measured and from the measured value thereof the presence or absence of the broken piece, the size of the broken piece or the amount of the broken piece accumulated is measured, the status (the presence or absence or the size) of the broken piece admixed in the fluid such as, for example, a lubricant oil, which is an object to be examined, can be estimated. Also, since where the broken piece detecting sensor assembly is incorporated in, for example, an automotive vehicle, an aircraft or a helicopter, the status of the broken piece admixed in the lubricant oil can be monitored, a diagnosis of a trouble or of the incipiency of occurrence of any trouble can be performed so that the necessity to halt the operation and/or the necessity of replacement of component parts can be acknowledged. Also, from the detected information, such information can be obtained before a destructive trouble occurs as a result of deterioration and/or damage.

In the present invention, the measuring and determining section is operable to measure the distance between the two flat plates in terms of capacitance. According to the capacitance, the distance between the two flat plates can be measured with a simplified structure and with high accuracy.

In the present invention, the measuring and determining section may estimate the capacitance by applying an alternating current and measuring an impedance. According to the impedance measurement, the measurement can be accomplished with a simplified structure and with high accuracy.

In the present invention, the measuring and determining section may include an oscillator for converting a change of the capacitance into a change of frequency and a frequency dependent capacitance estimator for estimating the capacitance from the frequency oscillated by the oscillator. Where the oscillator and the frequency dependent capacitance estimator are employed, it is possible to detect with high accuracy.

In the present invention, the measuring and determining section may include a charging and discharging device for repetitively inducing charge and discharge between the flat plates and a charge and discharge time dependent capacitance estimator for estimating the capacitance from a charge and discharge time induced by a transient phenomenon in repetition of charge and discharge. The provision of the charge and discharge time dependent capacitance estimator is also effective to allow the detection to be accomplished with high accuracy.

In the present invention, the measuring and determining section for measuring the distance between the two flat plates includes a displacement sensor. According to this construction, since by operating one of the two flat plates, the distance between the two flat plates is measured by the displacement sensor and from this measured value the presence or absence of the broken piece, the size of the broken piece or the amount of the broken piece accumulated is determined, the status of the broken piece (the presence or absence of or the size of the broken piece) can be detected accurately regardless of characteristics of the material, i.e., regardless of whether the broken piece admixed in the lubricant oil or the like, which is an object to be examined, is made up of the broken remains of metallic or non-metallic material, magnetic or non-magnetic material or electroconductive or non-electroconductive material.

In the present invention, an insulating layer may be provided on at least one of the two flat plates. According to this construction, since the insulating layer is provided on at least one of the two flat plates, the status of the broken piece can be assuredly estimated even where the broken piece sandwiched between those two flat plates is made up of broken remains of electroconductive material.

In the present invention, at least one of the flat plates may be supported by a support member having a flexibility sufficient to permit such one of the flat plates to tilt or any other construction may be employed and, for example, the entirety may be made in the form of an elastic body. The term "having a flexibility" referred to above and hereinafter is intended to mean having an elasticity or flexibility or the both. Also, the support member may be capable of softly recessing, in addition to tilting capability, that is, capable of retracting. According to this construction, when the broken piece is sandwiched between the two flat plates by operating one of the two flat plates and the distance between those two flat plates is measured by the measuring and determining section, the presence or absence of the broken piece or the size of the broken piece or the amount of the broken piece accumulated can be detected and since at least one of those two flat plates is fixedly supported by the support member having the flexibility, even when a plurality of particles of broken piece of, for example, varying size are sandwiched between the two flat plates, at least one of the flat plates can be brought into contact with the broken piece in a tilted, but stabilized posture due to the flexibility or elasticity of the flexible support member. For these reasons, the measured value given by the measuring and determining section will be stabilized and the presence or absence of, the size of or the amount of the broken piece accumulated in the fluid can be stably detected.

In the present invention, the support member supporting one of the two flat plates that is movable may have a coupling member capable of providing a freedom in a direction of tilting of such one of the flat plates. This coupling member stands for a member having its opposite ends rendered to be a joint to any other member and an intermediate portion having a flexibility so that it can be bendable. Where such a coupling member is employed, to secure a large freedom in a direction of tilting of the flat plate and to increase the degree of flexibility can be easily accomplished.

In the present invention, each of the two flat plates may be employed in the form of an electrode and further include an additional electrode, and wherein the shift mechanism moves at least one of the three electrodes to sandwich the broken piece between it and any one of the rest of the electrodes, and the measuring and determining section measures the size of a gap, defined as a distance between the two electrodes, sandwiching the broken piece therebetween. According to this construction, since by moving at least one of the three electrodes with the shift mechanism, the broken piece can be sandwiched between any two of the electrodes and by measuring the gap between the electrodes then sandwiching the broken piece therebetween, the presence or absence of, the size of or the amount of the broken piece accumulated can be detected, the probability of the broken piece being sandwiched between two of the electrodes is high and the presence or absence of the broken piece, the size of the broken piece or the amount of the broken piece accumulated can be stably detected without being adversely affected by the amount of the broken piece being admixed.

In the present invention, those three electrodes may be arranged one above the other in a vertical direction and a gap measuring device may be disposed between upper two of those electrodes and between lower two of those electrodes, the shifting mechanism being operable to move one of the electrodes, which is positioned intermediate between the other two electrodes, up and down to sandwich the broken piece between the upper two electrodes and between the lower two electrodes. In the case of this construction, respective detecting operations can be accomplished at opposite ends of the single stroke of movement of the intermediate electrode and, therefore, the efficiency of the detecting operation can also be increased.

In the present invention, the shift mechanism for moving such one of the electrodes positioned intermediate between the other two electrodes may be disposed outside a liquid passage through which the fluid flows and the shift mechanism moves such one of the electrodes, positioned intermediate between the other two electrodes, through an insert body extending through a hole defined in one of the two electrodes on a stationary side. In the case of this construction, the three electrodes can be arranged compactly.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

FIG. 1 is a schematic structural diagram showing a broken piece detecting sensor assembly according to a first preferred embodiment of the present invention in a condition when the sensor assembly is electrically powered on;

FIG. 7 is a schematic structural diagram showing a broken piece detecting sensor assembly according to a second preferred embodiment of the present invention in a condition when the sensor assembly is electrically powered on;

FIG. 8 is a schematic structural diagram showing a broken piece detecting sensor assembly according to a third preferred embodiment of the present invention in a condition when the sensor assembly is electrically powered on;

FIG. 13 is a schematic structural diagram showing the detecting operation of the broken piece detecting sensor assembly according to a sixth preferred embodiment of the present invention in a condition when the sensor assembly is electrically powered on;

FIG. 17 is a schematic structural diagram showing the detecting operation of the broken piece detecting sensor assembly according to a seventh preferred embodiment of the present invention in a condition when the sensor assembly is electrically powered on;

FIG. 18 is a schematic structural diagram showing the detecting operation of the broken piece detecting sensor assembly according to an eighth preferred embodiment of the present invention in a condition when the sensor assembly is electrically powered on;

FIG. 24 is a schematic structural diagram showing the detecting operation of the broken piece detecting sensor assembly according to an eleventh preferred embodiment of the present invention operating under a first mode when the sensor assembly is electrically powered on;

FIG. 26 is a schematic structural diagram showing the broken piece detecting sensor assembly according to the eleventh preferred embodiment operating under a second mode when the latter is electrically powered on;

DETAILED DESCRIPTION OF THE EMBODIMENTS

Figure 1:
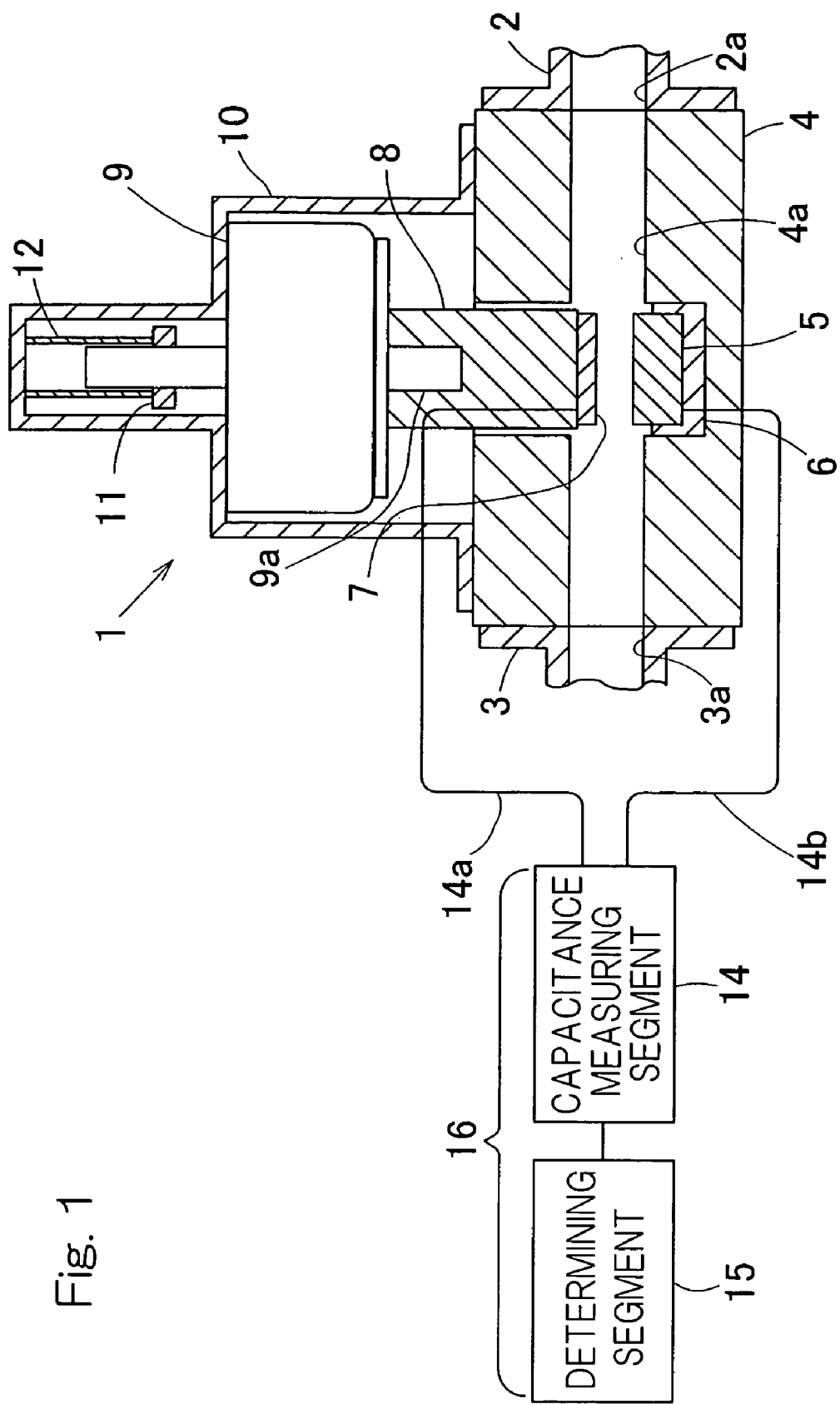

A first preferred embodiment of the present invention will be described in detail with particular reference to FIGS. 1 to 4. FIG. 1 illustrates a schematic structural diagram of the broken piece detecting sensor assembly according to the first embodiment of the present invention. This broken piece detecting sensor assembly detects a broken piece admixed in a fluid, which is an object to be examined, and includes two flat plates 5 and 7 confronting each other, a shift mechanism 9 for moving at least one of the two flat plates 5 and 7 in a direction in which they confront, to allow broken piece 13 (FIG. 3) to be sandwiched between the flat plates 5 and 7, and a measuring and determining section 16 for measuring a distance between the two flat plates 5 and 7 and then detecting the presence or absence of the broken piece 13, the size thereof or the amount thereof accumulated. In the case of this broken piece detecting sensor assembly, a lubricant oil, which is a kind of fluid, is chosen to be a fluid that is an object to be examined.

The two flat plates 5 and 7 and the shifting mechanism 9 are incorporated in a sensor unit 1. This sensor unit 1 includes a base member 4 having an oil flow path 4a defined therein forming a flow path for the lubricant oil forming an object to be examine, and the oil flow path 4a has one end fluidly connected with an oil supply tube 2 and the opposite end fluidly connected with an oil discharge tube 3. In this case, the lubricant oil flows from an oil passage 2a, defined in the oil supply tube 2, towards an oil passage 3a, defined in the oil discharge tube 3, through the oil flow path 4a in the base member 4. By way of example, the oil supply tube 2 is fluidly connected with a piping, where the lubricant oil having been used in a combustion engine, a gear box and/or bearing assemblies is collected, and the oil discharge tube 3 is fluidly connected with an oil tank.

Of the two flat plates 5 and 7, the flat plate 5 is a stationary flat plate made of an electroconductive material and is positioned generally intermediate of the oil flow path 4a in the base member 4 and secured to the base member 4 in electrically insulated relation therewith through a fixing member 6 made of an insulating material. The stationary flat plate 5 has one surface thereof and is so positioned with its surface oriented towards the oil flow path 4a.

The shifting mechanism 9 is in the form of a direct acting actuator such as, for example, a push-pull solenoid and has a movable shaft 9a. This shifting mechanism 9 is fixed to the base member 4 through an actuator fixing member 10 so that the movable shaft 9a thereof can reciprocatingly move in a direction perpendicular to the direction in which the oil flow path 4a extends within the base member 4. The movable shaft 9a of the direct acting actuator 9 has a free end fixed to one of the two flat plates 5 and 7, for example, the flat plate 7 in the illustrated instance, through a fixing member 8, made of an insulating material, in electrically insulated relation therewith. This flat plate 7 is a movable flat plate reciprocatingly movable together with the movable shaft 9a of the direct acting actuator 9 and is made of an electroconductive material in a manner similar to the stationary flat plate 5. This flat plate 7 can move into the oil flow path 4a, having traversed the base member 4, so as to terminate in face-to-face relation with the stationary flat plate 5. Although in the illustrated instance the push-pull solenoid has been used as the direct acting actuator 9, any direct acting actuator may be employed. By way of example, a combination of an electrically driven motor and a ball screw may be employed therefor, or it may be of either a hydraulically operated type utilizing a hydraulic pressure or a pneumatically operated type utilizing a pneumatic pressure. Where the direct acting actuator is employed for the shifting mechanism 9, unlike the actuator employing a rotary drive source, no mechanism for translating a rotary motion into a rectilinear motion is required and, accordingly, the broken piece detecting sensor assembly can be assembled compact in structure. When the direct acting actuator 9 is operated, the movable flat plate 7 coupled with the movable shaft 9a through the fixing member 8 moves reciprocatingly in a direction close towards and away from the stationary flat plate 5.

Figure 2:
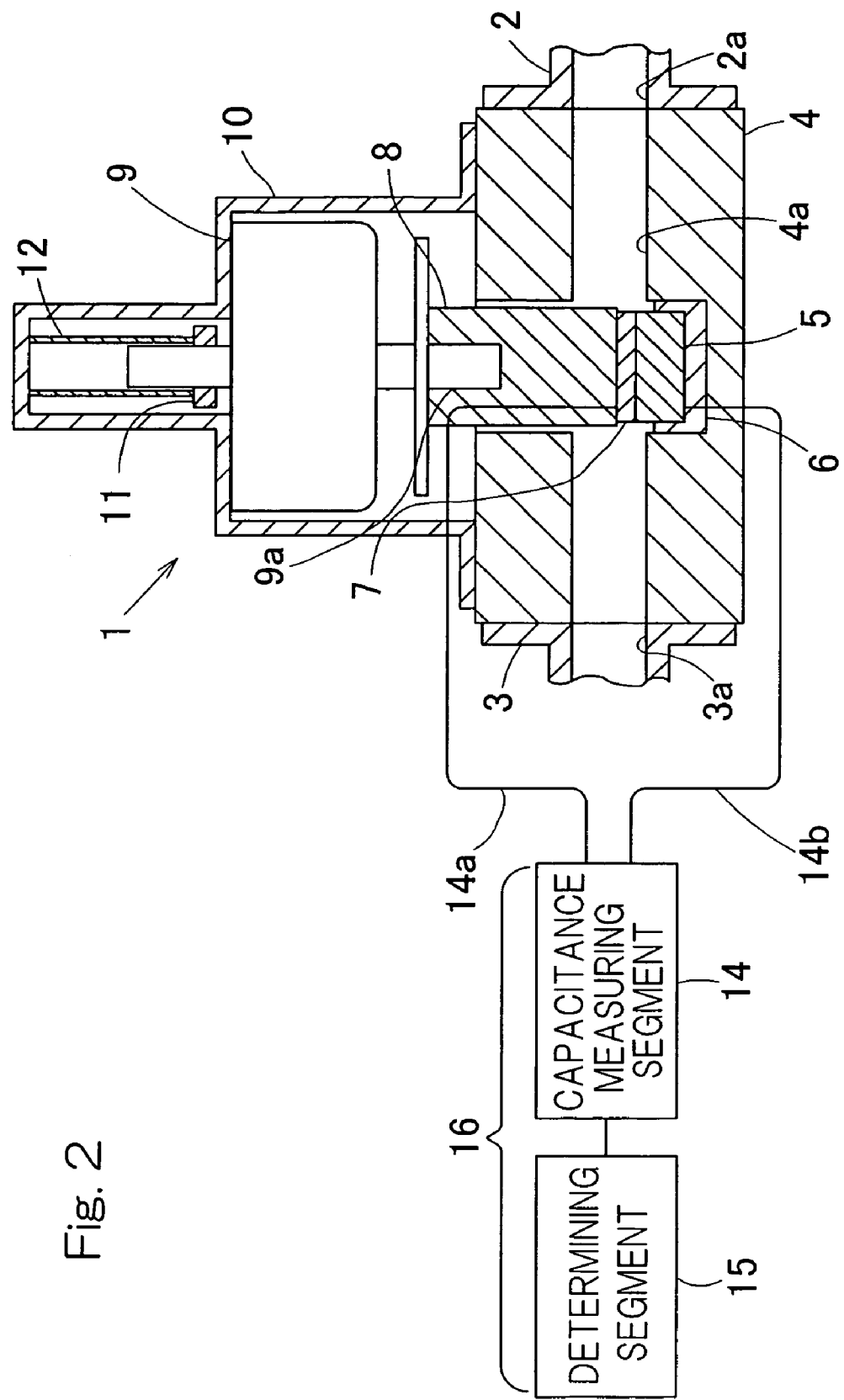
FIG. 2 is a schematic structural diagram showing the broken piece detecting sensor assembly according to the first preferred embodiment in a condition when the supply of an electric power is halted.
Figure 3:
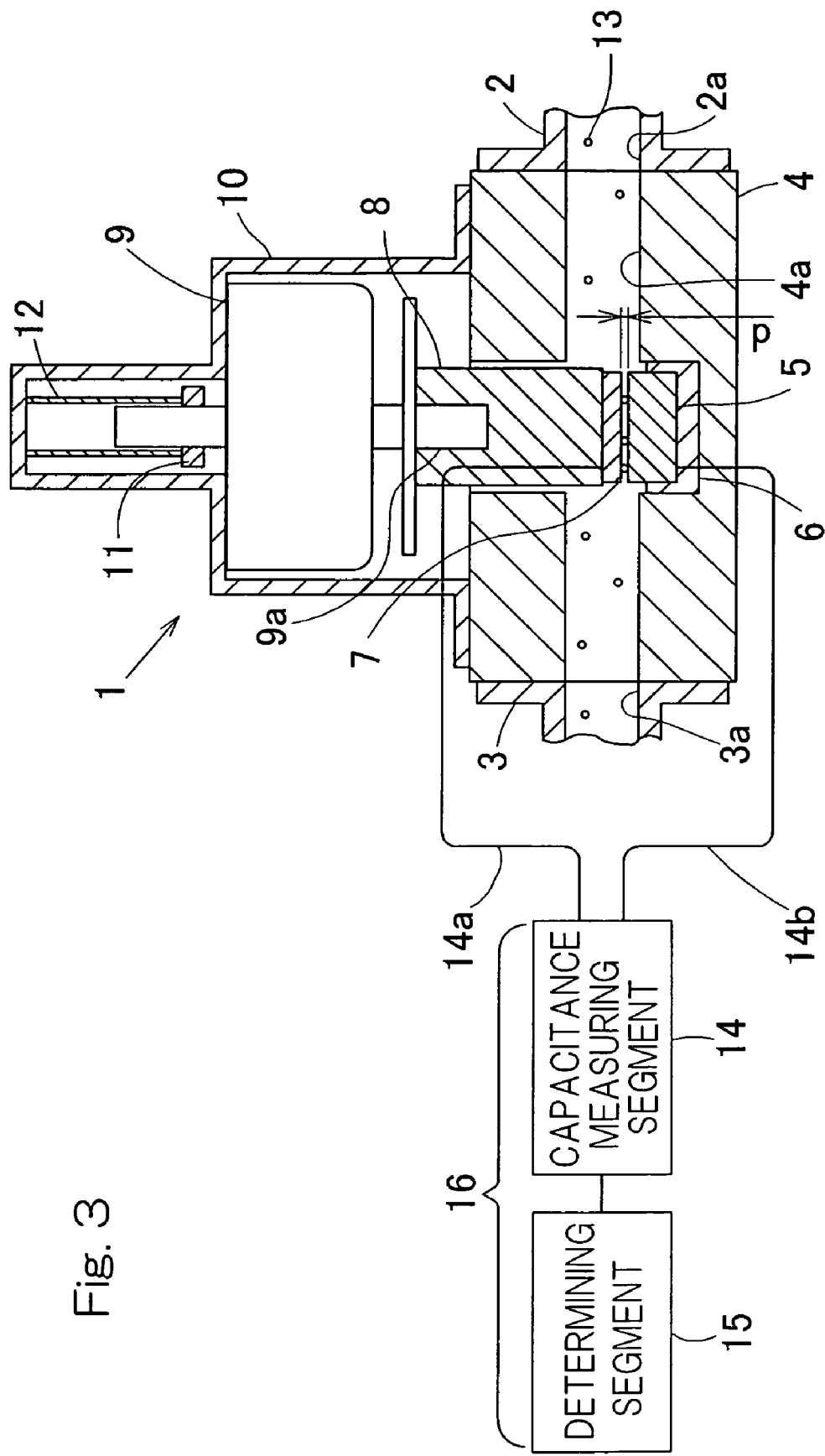
FIG. 3 is an explanatory diagram showing the detecting operation performed by the broken piece detecting sensor assembly according to the first preferred embodiment.

The movable shaft 9a of the direct acting actuator 9 is normally biased to assume an advanced position by the action of a compression spring 12 interposed between a spring catch 11, secured to a rear end of the movable shaft 9a, and the actuator fixing member 10. FIG. 1 illustrates the direct acting actuator 9 then electrically powered on, at which time the movable shaft 9a is retracted to assume a retracted position with the compression spring 12 axially inwardly compressed, allowing the movable flat plate 7 to be positioned away from the stationary flat plate 5. On the other hand, in a condition in which the direct acting actuator 9 is not electrically powered on with no electrical power supplied thereto, the movable flat plate 7 is moved to the advanced position, where the movable flat plate 7 is brought into contact with the stationary flat plate 5 as shown in FIG. 2, by the effect of a resilient restoring force which is accumulated in the compression spring 12 when the direct acting actuator 9 was electrically powered on. In the condition in which the movable flat plate 7 is held in contact with the stationary flat plate 5, a preload is applied to the movable flat plate 7 by the compression spring 12 and, therefore, the movable flat plate 7 and the stationary flat plate 5 are held in contact with each other under a predetermined and constant pressure.

Measuring and determining section 16 includes a capacitance measuring segment 14 and a determining segment 15. The capacitance measuring segment 14 measures the capacitance between the movable flat plate 7 and the stationary flat plate 5 and has electrodes 14a and 14b connected with the movable flat plate 7 and the stationary flat plate 5, respectively, which electrodes 14a and 14b define respective input terminals of the capacitance measuring segment 14. The determining segment 15 determines the status of broken piece 13 (FIG. 3) within the lubricant oil in reference to a measured value given by the capacitance measuring segment 14 and includes a determining rule in the form of, for example, a table or a calculating equation defining the relationship between the measured value and the result of determination so that by comparing the measured value with the determining rule, a result of determination concerning the presence or absence of the broken piece, the size of the broken piece or the amount of the broken piece accumulated can be outputted therefrom.

In the following description, the operation to detect the presence or absence of broken piece in the lubricant oil containing the broken piece of various materials, which has resulted from frictional wear and/or breakage of, for example, a combustion engine, a gear box and/or bearing assemblies with the use of the broken piece detecting sensor assembly of the structure described above, will be described. When the direct acting actuator 8 is electrically powered on as hereinbefore described, the movable shaft 9a retracts as shown in FIG. 1 and, accordingly, the movable flat plate 7 coupled with the movable shaft 9a through the fixing member 8 separates away from the stationary flat plate 5. At this time, the compression spring 12 interposed between the spring catch 11, secured to the movable shaft 9a, and the actuator fixing member 10 is compressed axially inwardly.

When the direct acting actuator 9 is halted with no electric power supplied thereto while a lubricant oil as a fluid to be examined, used in the combustion engine, the gear box and/or the bearing assemblies is supplied to flow from the oil passage 2a in the oil supply tube 2 towards the oil passage 3a in the oil discharge tube 3 through the oil flow path 4a in the base member 4, the movable flat plate 7 moves towards the advanced position together with the movable shaft 9a by the effect of the resilient restoring force accumulated in the compression spring 12. Where at this time the broken piece 13 of the various materials resulting from the frictional wear and/or breakage of the combustion engine, the gear box and/or the bearing assemblies is admixed in the lubricant oil then flowing through the oil flow path 4a in the base member 4, the broken piece 13 is sandwiched between the movable flat plate 7 and the stationary flat plate 5, forming therebetween the distance (gap) d corresponding to the thickness of the broken piece 13 so sandwiched. The presence of the gap d between the movable and stationary flat plates 7 and 5 forms a capacitance C thereacross.

In the meantime, the capacitance C between parallel flat plates is generally known as expressed by the following equation.

$$C = \epsilon_o \cdot \epsilon_r \cdot S/d \quad (1)$$

In other words, the capacitance C [F] is represented by the product of the dielectric constant $\epsilon_o$ (=8.854×10$^{-12}$ [F/m]) in the vacuum times the dielectric constant $\epsilon_r$ of the lubricant times the surface area S [m$^2$] of the parallel flat plates, which is then divided by the gap d [m] between the parallel flat plates. In the case of the illustrated embodiment, since the dielectric constant $\epsilon_r$ of the lubricant and the surface area S of the parallel flat plates are constant, the capacitance C depends on the gap d between the parallel flat plates, that is, between the movable flat plate 7 and the stationary flat plate 5. In view of this, when the capacitance C between the two flat plates 5 and 7 is measured by the capacitance measuring segment 14, the value of the gap d between the flat plates 5 and 7 can be detected, from which the size of or the amount of the broken piece 13 accumulated can be estimated.

On the other hand, where no broken piece 13 is present between the two flat plates 5 and 7, the gap d of a very micro size is formed in the presence of the lubricant oil between those flat plates 5 and 7, or the flat plates 5 and 7 are held in contact with each other. In the case of the gap d of the very micro size attributable to the lubricant oil, the capacitance C exhibits a considerably high value when compared with that exhibited by the presence of the broken piece 13 between the flat plates 5 and 7. On the other hand, when the flat plates 5 and 7 are held in contact with each other, an electroconductive circuit is established therebetween. Accordingly, the presence or absence of the broken piece 13 can be determined from those values. Determination of the presence or absence of, the size of or the amount of the broken piece 13 accumulated can be accomplished by the determining segment 15 based on the measured value given by the capacitance measuring segment 14. The capacitance measuring segment 14 may be employed in the form of a measuring instrument such as, for example, an electric capacitance meter.

Figure 4:
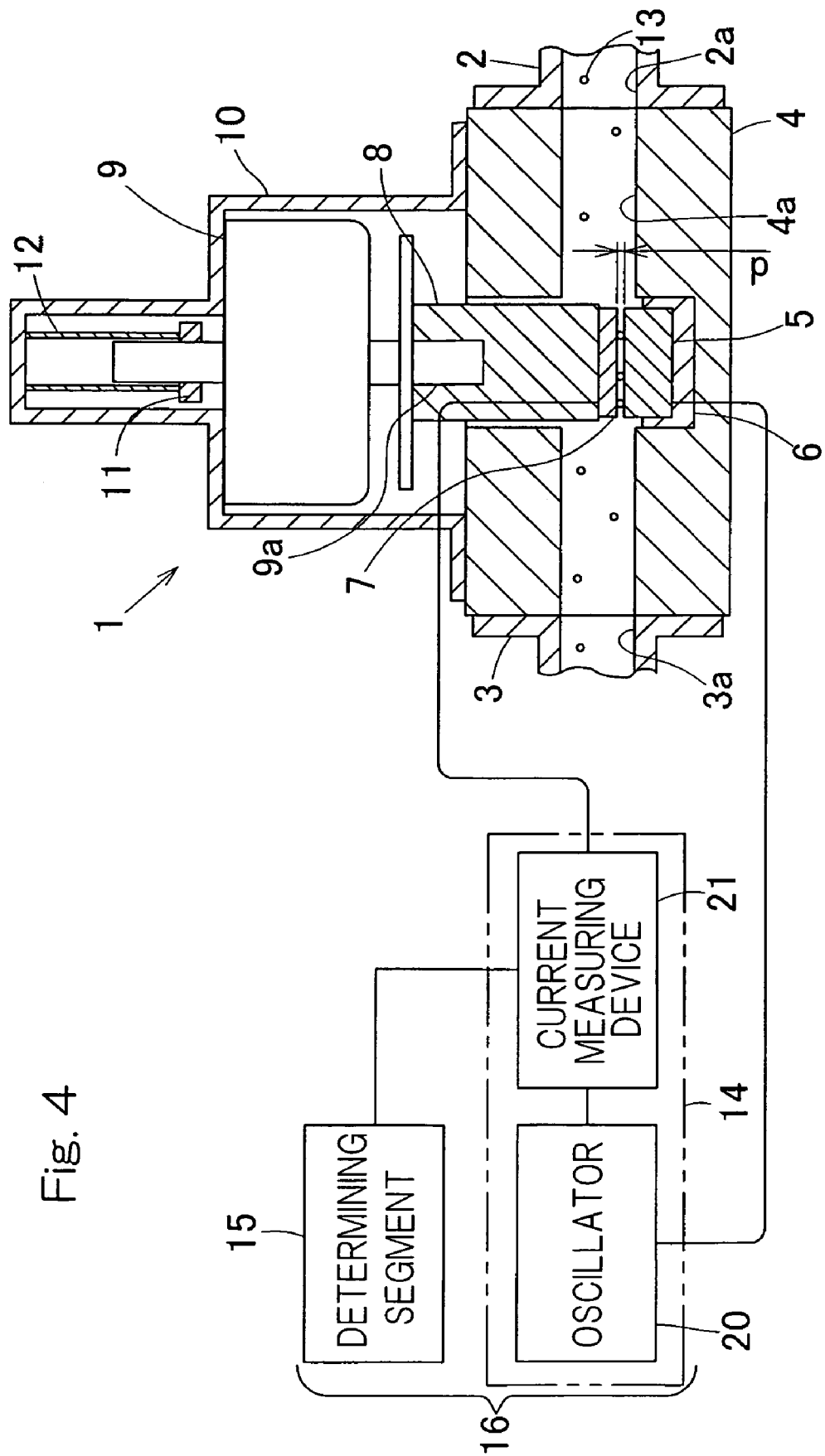
FIG. 4 is an explanatory diagram showing the detecting operation which takes place when a first constructional example of a capacitance measuring segment is utilized in the broken piece detecting sensor assembly according to the first preferred embodiment.

FIG. 4 illustrates a first constructional example of the capacitance measuring segment 14, which forms a part of the measuring and determining section 16 of the broken piece detecting sensor assembly shown in and described with reference to FIG. 1. This capacitance measuring segment 14 includes an oscillator 20 and a current measuring device 21 connected in series with the oscillator 20 and is so designed and so configured that the oscillator 20 may supply an alternating current to the movable flat plate 7 and the stationary flat plate 5 and the current measuring device 21 may measure the capacitance C between the flat plates 5 and 7 in terms of the impedance. In this case, the capacitance C can be determined from the impedance so measured by the current measuring device 21. Other structural features than those described above are similar to those shown in and described with reference to FIG. 1.

Figure 5:
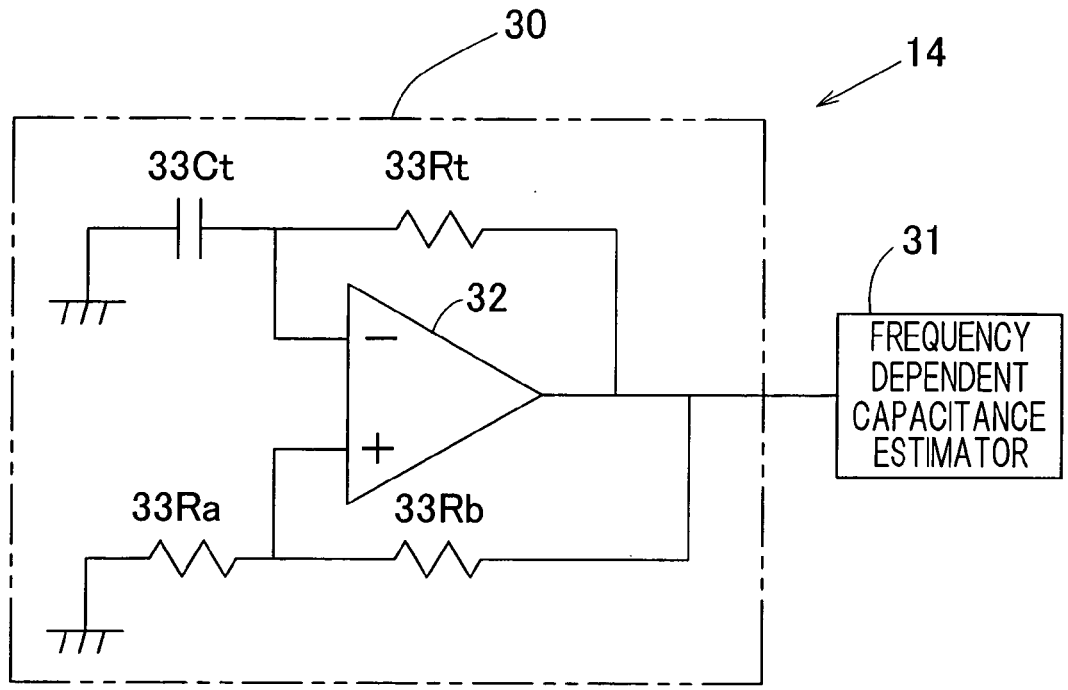
FIG. 5 is a circuit diagram showing a second constructional example of the capacitance measuring segment employed in the broken piece detecting sensor assembly according to the first preferred embodiment.

A circuit diagram shown in FIG. 5 illustrates a second constructional example of the capacitance measuring segment employed in the broken piece detecting sensor assembly. The capacitance measuring segment 14 shown therein takes the place of the capacitance measuring segment 14, which forms a part of the measuring and determining section 16 employed in the broken piece detecting sensor shown in and described with reference to FIG. 4, and includes an oscillator 30 in the form of an OP amplifier 32 and a frequency dependent capacitance estimator 31 for estimating the capacitance from the frequency oscillated by the oscillator 30. This capacitance measuring segment 14 is operable to estimate the capacitance C between the flat plates 5 and 7 (FIG. 4) from the frequency of the oscillator 30 measured. The oscillator 30 employed in this instance is called a relaxation oscillator and includes resistors 33Ra, 33Rb and 33Rt and a capacitor 33Ct all connected with the OP amplifier 32 as shown. Assuming that the resistances of the resistors 33Ra, 33Rb and 33Rt are expressed by Ra, Rb and Rt, respectively, and the capacitance of the capacitor 33Ct is expressed by Ct, it is known that the oscillating frequency f is about equal to the value expressed by the following equation.

$$F = 1/(2Rt \cdot Ct) \quad (2)$$

Here, where the capacitance Ct of the capacitor 33Ct of the oscillator 30 is replaced with the capacitance C between the flat plates 5 and 7, the capacitance C thereof can be estimated.

Figure 6:
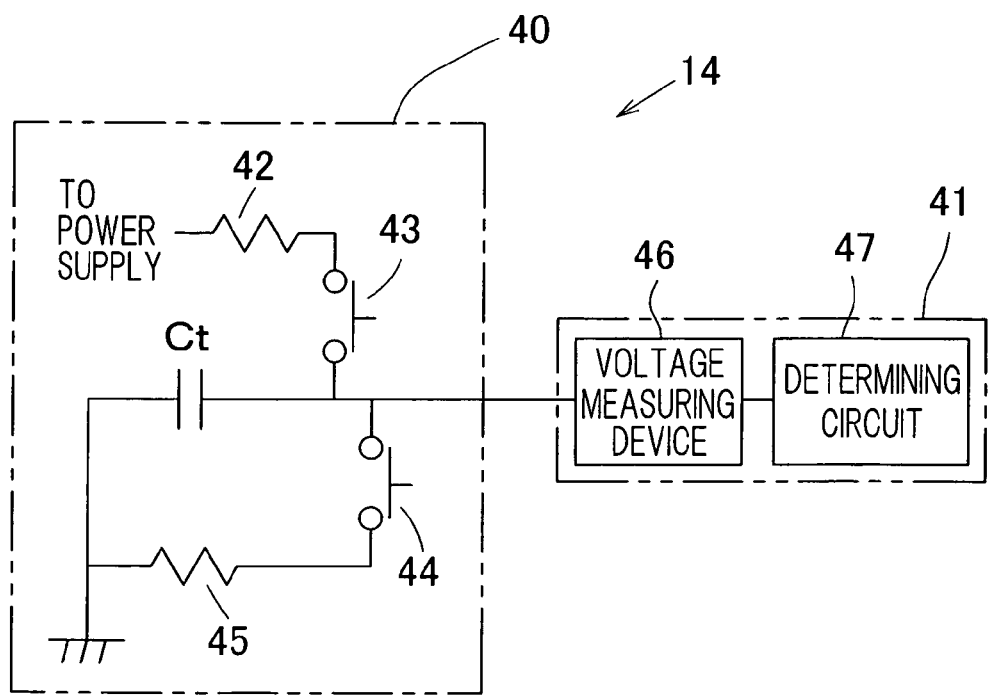
FIG. 6 is a circuit diagram showing a third constructional example of the capacitance measuring segment employed in the broken piece detecting sensor assembly according to the first preferred embodiment.

The circuit shown in FIG. 6 illustrates a third constructional example of the capacitance measuring segment employed in the broken piece detecting sensor assembly. The capacitance measuring segment 14 shown therein also takes the place of the capacitance measuring segment 14, which forms a part of the measuring and determining section 16 employed in the broken piece detecting sensor shown in and described with reference to FIG. 4, and includes a charging and discharging device 40 and a charge and discharge time dependent capacitance estimator 41 capable of estimating the capacitance by means of the charge and discharge time during a transient phenomenon in repetition of charge and discharge. The charging and discharging device 40 is a circuit in which a series connected circuit including a charge resistor 42 and a charge switch 43 connected in series with such charge resistor is connected in series with a to-be-measured capacitance Ct and, also, a series connected circuit including a discharge switch 44 and a discharge resistor 45 connected in series with the discharge switch 44 is connected in parallel to the to-be-measured capacitance Ct. This charge and discharge time dependent capacitance estimator 41 includes a voltage measuring device 46 for monitoring the charge and discharge voltage at the charging and discharging device 40 and a determining circuit 47 for determining the to-be-measured capacitance Ct by measuring the length of time required for the voltage, monitored by the voltage measuring device 46, to attain a value equal to a predetermined voltage.

In the case of this third constructional example, when after the charge switch 43 has been turned on to initiate the charging the voltage charged on the to-be-measured capacitance Ct is monitored by the voltage measuring device 46 and, at the same time, the length of time required for the voltage to attain a value equal to the predetermined voltage is measured by the determining circuit 47, the to-be-measured capacitance Ct can be estimated. Also, with respect to the to-be-measured capacitance Ct charged to a predetermined voltage, when after the discharge switch 44 has been switched on to initiate the discharge the discharge voltage of the to-be-measured capacitance Ct is monitored by the voltage measuring device 46 and, at the same time, the length of time required for the discharge voltage thereof to attain a value equal to the predetermined voltage is measured by the determining circuit 47, the to-be-measured capacitance Ct can be estimated. Here, if the to-be-measured capacitance Ct referred to above is replaced with the capacitance C between the flat plates 5 and 7 (FIG. 4), the capacitance C thereof can be estimated.

As described above, since the broken piece detecting sensor assembly according to the first embodiment of the present invention is so designed and so configured that the movable flat plate 7 can be moved to allow the capacitance measuring segment 14 to measure the capacitance C between the movable flat plate 7 and the stationary flat plate 5 so that the presence or absence of the broken piece 13, the size of the broken piece 13 or the amount of the broken piece 13 accumulated can be determined by the determining segment 15 in reference to the measured value given by the capacitance measuring segment 14, the status of the broken piece 13 admixed in the lubricant oil can be estimated. Also, where the broken piece detecting sensor referred to above is incorporated in, for example, an automotive vehicle, an aircraft or a helicopter, the status of the broken piece admixed in the lubricant oil can be monitored and, therefore, a diagnosis of a trouble or of the incipiency of occurrence of any trouble can be performed so that the necessity to halt the operation and/or the necessity of replacement of component parts can be acknowledged, resulting in increase of the safety. In addition, since the lifetime and time dependent change of mechanical component parts can be predicated, unnecessary replacement of component parts and/or delay in replacement can be alleviated, resulting in increase of the economy.

Figure 7:
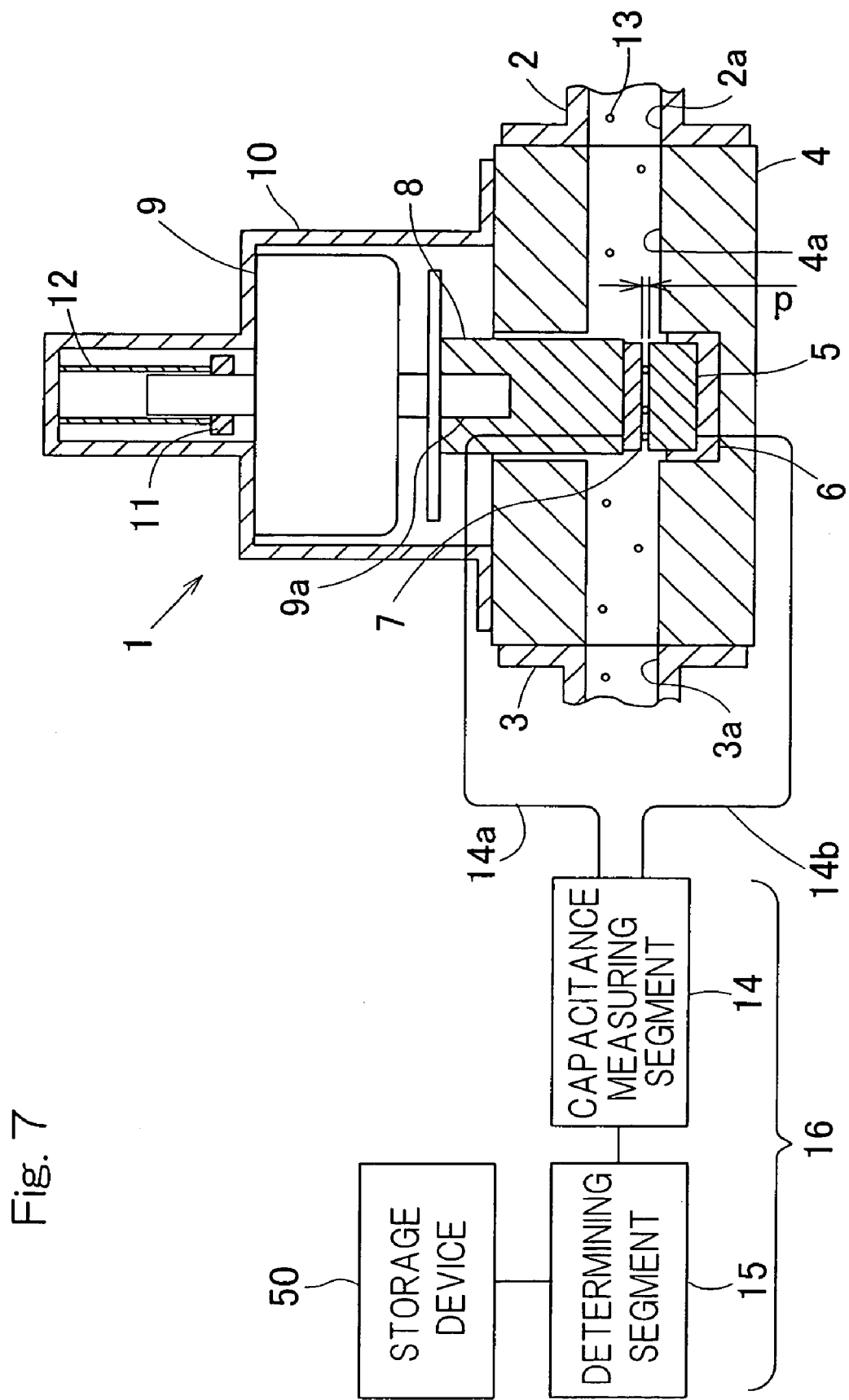

FIG. 7 illustrates a schematic structural diagram showing the broken piece detecting sensor assembly according to a second preferred embodiment of the present invention in a condition when the sensor assembly is electrically powered on. This second embodiment is similar to the first embodiment shown in and described with reference to FIG. 1, except that in accordance to the second embodiment, a storage device 50 is added to the stage next to the determining segment 15 employed in the first embodiment so that the status of the broken piece 13 admixed in the lubricant oil can be monitored in real time. The capacitance measuring segment 14 may be identical with that shown in and described with reference to any one of FIGS. 4 to 6. It is to be noted that the determining segment 15 may be of a type capable of determining the occurrence of an inconvenience when the extent to which the capacitance measured by the capacitance measuring segment 14 changes exceeds a predetermined threshold value.

Figure 8:
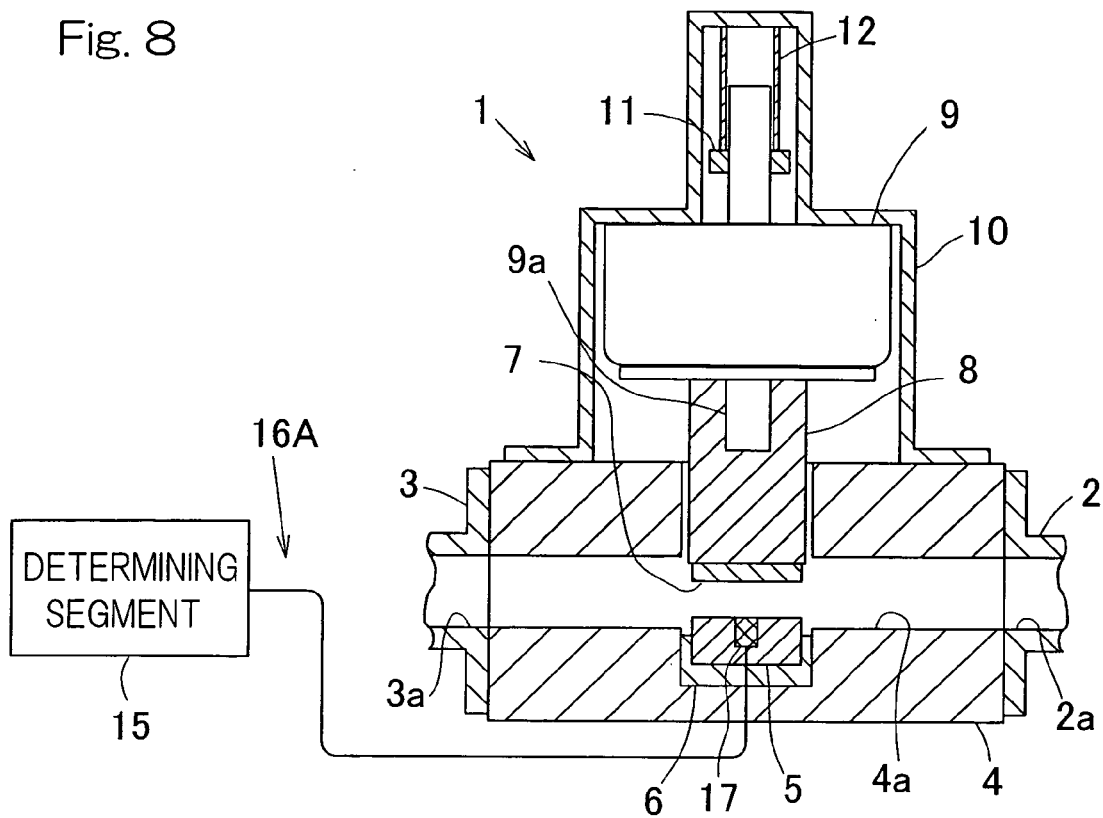
Figure 9:
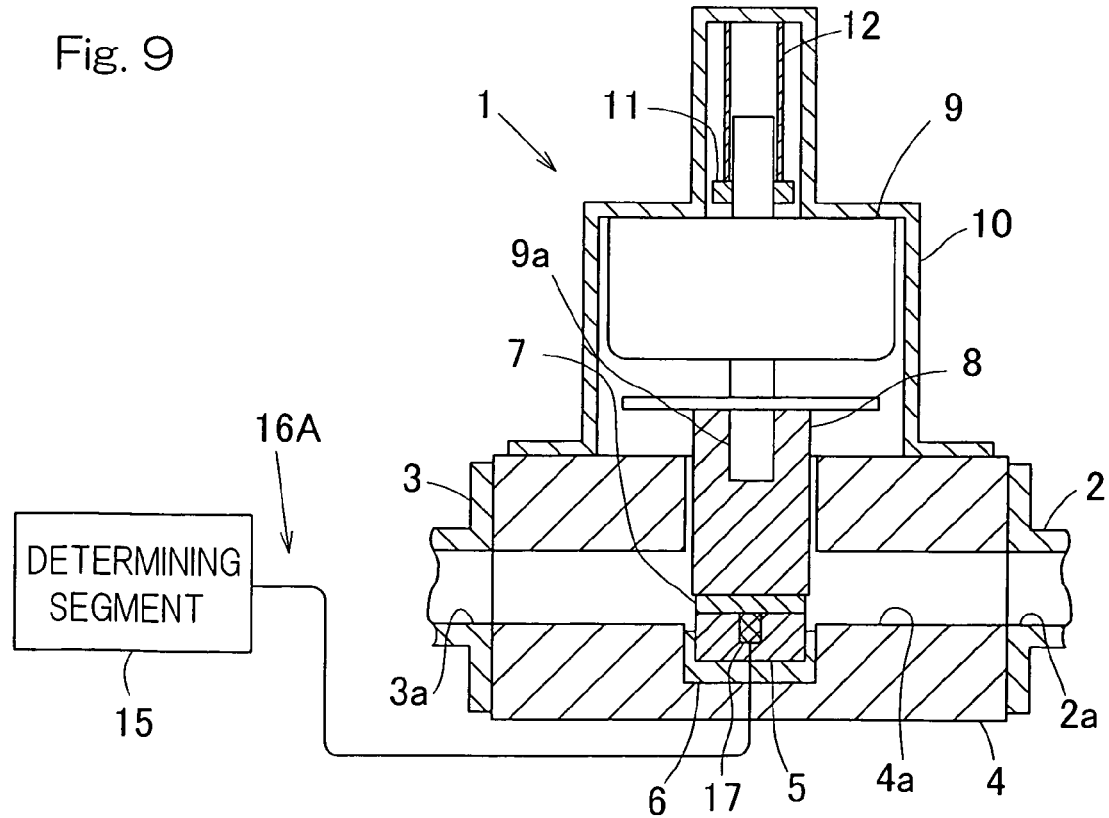
FIG. 9 is a schematic structural diagram showing the broken piece detecting sensor assembly according to the third preferred embodiment in a condition when the supply of an electric power is halted.

A third preferred embodiment of the present invention will be hereinafter described with particular reference to FIGS. 8 and 9. The schematic structure of the broken piece detecting sensor assembly according to this third embodiment is substantially similar to that according to the first embodiment shown in and described with reference to FIG. 1 and, therefore, like parts are designated by like reference numerals and the details are not reiterated for the sake of brevity except that only differences of the third embodiment that depart from the first embodiment are discussed. FIG. 8 is a schematic structural diagram showing the broken piece detecting sensor assembly according to this third embodiment in a condition when the direct acting actuator 9 is electrically powered on, and in this condition, the movable shaft 9a is held in the retracted position with the compression spring 12 compressed axially and with the movable flat plate 7 held at a position separated from the stationary flat plate 5. On the other hand, as shown in FIG. 9, in a condition in which the direct acting actuator 9 is not electrically powered on, the movable flat plate 7 is held in the advanced position contacting the stationary flat plate 5 by the effect of the resilient restoring force accumulated in the compression spring 12 which had compressed axially when the electric power was previously supplied to the direct acting actuator 9. Since while the movable flat plate is held in contact with the stationary flat plate 5 a preload is applied to the movable flat plate 7 by the compression spring 12, the movable plate 7 and the stationary plate 5 are held in contact with each other under a predetermined pressure.

As shown in FIG. 8, the measuring and determining section 16A employed in the practice of the third embodiment is made up of a displacement sensor 17 and a determining segment 15. The displacement sensor 17 measures the distance (gap) d between the movable flat plate 7 and the stationary flat plate 5 and is disposed having been, for example, embedded in the stationary flat plate 5. In the illustrated instance, the displacement sensor 17 is employed in the form of an eddy current type, but any other type such as, for example, a magnetic type or an optical type may be employed therefor. Specifically, where the displacement sensor 17 of, for example, the optical type is employed, both of the stationary flat plate 5 and the movable flat plate 7 may not be made of an electroconductive material, or it may be secured to either the base member 4 or the movable shaft 9a with none of the fixing members 6 and 8 intervening therebetween. The determining segment 15 determines the status of the broken piece 13 (FIG. 10), admixed in the lubricant oil, in reference to the measured value given by the displacement sensor 17 and includes a determining rule in the form of, for example, a table or a calculating equation defining the relationship between the measured value and the result of determination so that by comparing the measured value with the determining rule, a result of determination concerning the presence or absence of the broken piece, the size of the broken piece or the amount of the broken piece accumulated can be outputted therefrom.

Figure 10:
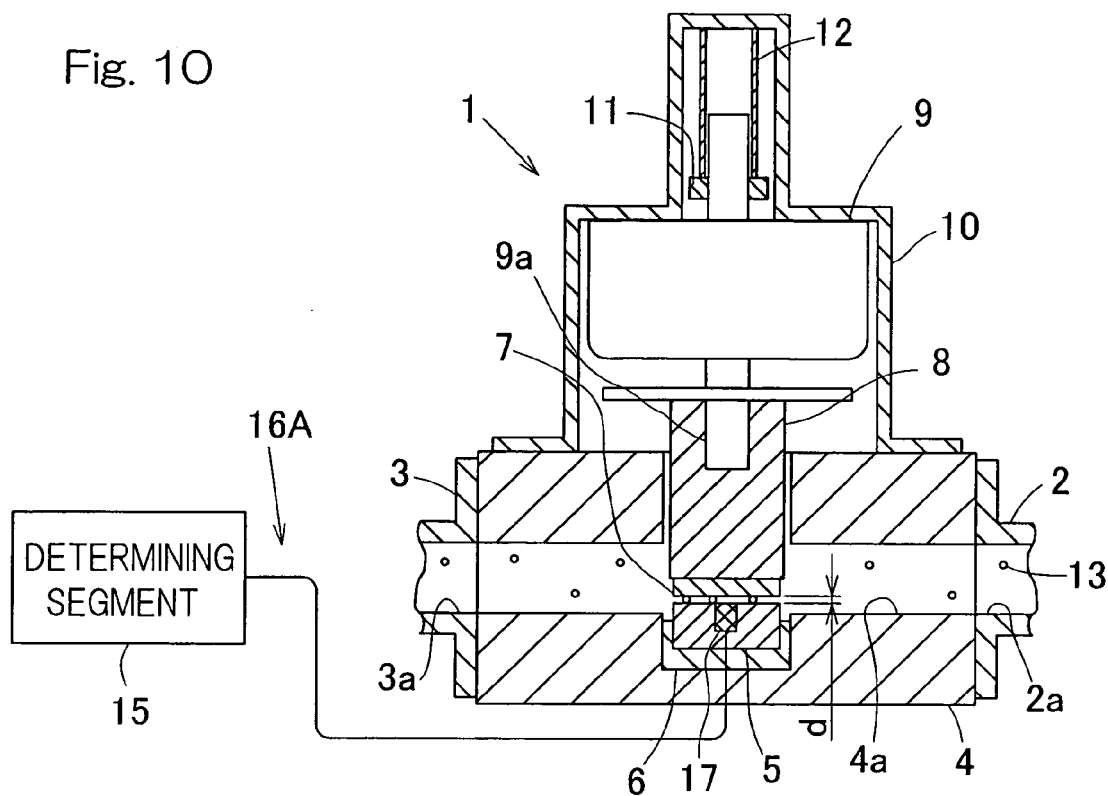
FIG. 10 is an explanatory diagram showing the detecting operation of the broken piece detecting sensor assembly according to the third preferred embodiment.

The detecting operation of the broken piece detecting sensor assembly according to this third embodiment to detect the broken piece contained in the lubricant oil takes place in a manner similar to that shown and described in connection with the first embodiment. As best shown in FIG. 10, in this third embodiment, the broken piece 13 is, if admixed in the lubricant oil, sandwiched between the movable flat plate 7 and the stationary flat plate 5. Accordingly, the gap (distance) d corresponding to the thickness of the broken piece 13 is formed between the movable flat plate 7 and the stationary flat plate 5. The displacement sensor 17 then measures this gap d and the determining segment 15 estimates the size of the broken piece 13 or the amount of the broken piece 13 accumulated in reference to the measured value given by the displacement sensor 17.

If no broken piece 13 is present between the two flat plates 5 and 7, either the gap d attributable to a very micro film of the lubricant oil is formed, or the two flat plates 5 and 7 are brought into contact with each other as is the case with the previously discussed first embodiment. In the case of the very micro gap of the lubricant oil present between the two flat plates 5 and 7, the measured value indicative of the gap d given by the displacement sensor 17 will be of an extremely low value as compared with that given when the broken piece 13 is sandwiched between the two flat plates 5 and 7. On the other hand, if the two flat plates 5 and 7 are brought into contact with each other, the measured value given by the displacement sensor 17 will be substantially zero. Accordingly, based on this result of measurement, the determining segment 15 can determine the presence or absence of the broken piece 13.

As hereinabove described, since the broken piece detecting sensor assembly according to the third embodiment of the present invention is so designed and so configured that the movable flat plate 7 can be moved to allow the displacement sensor 17 to measure the gap d between the movable flat plate 7 and the stationary flat plate 5 so that the presence or absence of the broken piece 13, the size of the broken piece 13 or the amount of the broken piece 13 accumulated can be determined by the determining segment 15 in reference to the measured value given by the displacement sensor 17, the status of the broken piece 13 admixed in the lubricant oil can be estimated regardless of the material characteristics of the broken piece 13, i.e., whether the material for the broken piece 13 is metallic or non-metallic, magnetic or non-magnetic, electroconductive or non-electroconductive.

Figure 11:
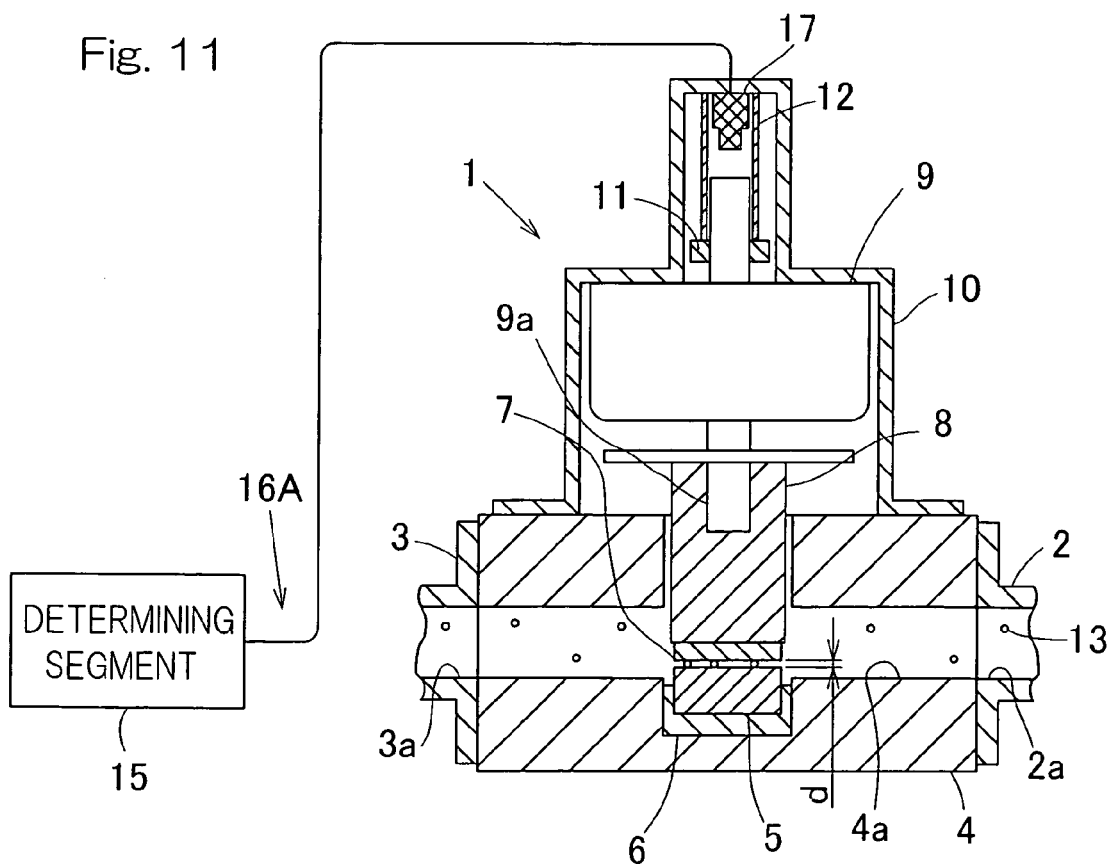
FIG. 11 is an explanatory diagram showing the detecting operation of the broken piece detecting sensor assembly according to a fourth preferred embodiment of the present invention.

FIG. 11 illustrates a fourth preferred embodiment of the broken piece detecting sensor assembly according to the present invention. In this fourth embodiment, the displacement sensor 17 shown and described as employed in the third embodiment described with particular reference to FIG. 8 is disposed within the actuator fixing member 10 at a location adjacent a rear end of the movable shaft 9a.

According to this fourth embodiment, the displacement sensor 17 measures the amount of displacement of the movable shaft 9a, but since the movable flat plate 7 is fixed to the movable shaft 9a through the flat plate fixing member 8, the gap d between the stationary flat plate 5 and the movable flat plate 7 can be detected in reference to the amount of displacement of the movable shaft 9a.

Figure 12:
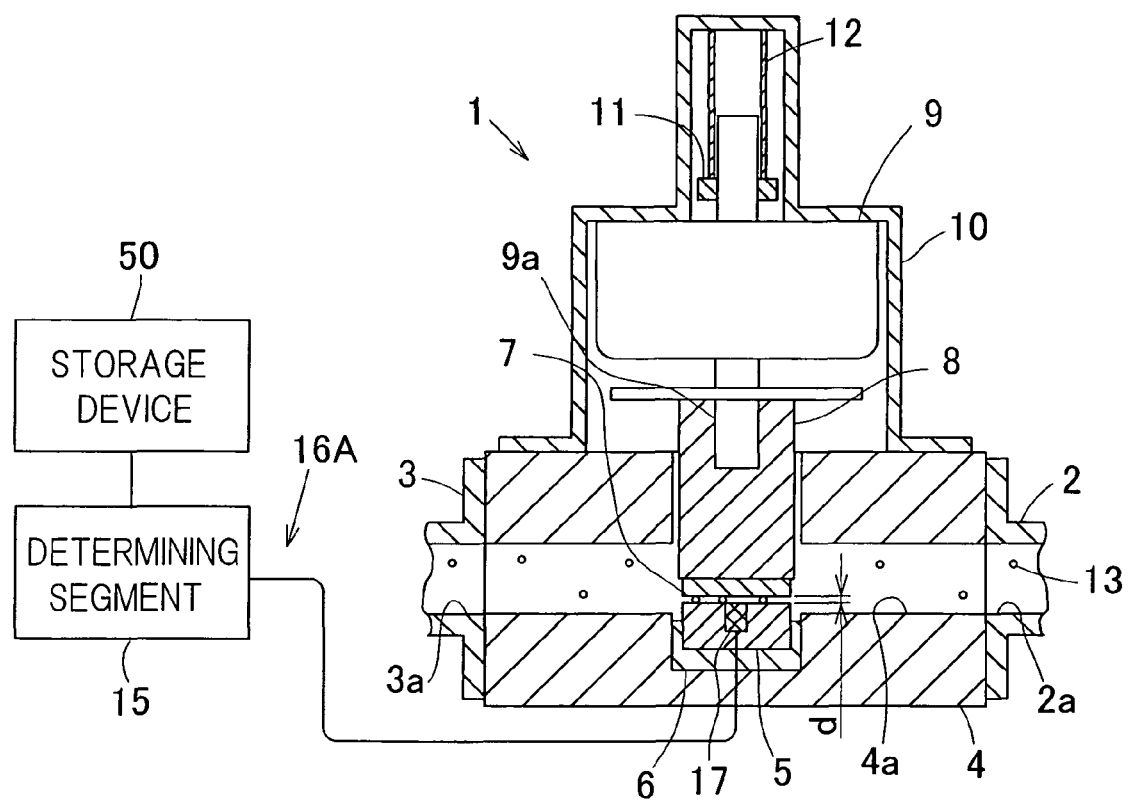
FIG. 12 is an explanatory diagram showing the detecting operation of the broken piece detecting sensor assembly according to a fifth preferred embodiment of the present invention.

FIG. 12 illustrates a fifth preferred embodiment of the broken piece detecting sensor assembly according to the present invention. In this fifth embodiment, a storage device 50 is added to the stage next to the determining segment 15 so that the status of the broken piece 13 admixed in the lubricant oil can be monitored in real time. It is to be noted that the determining segment 15 may be of a type capable of determining the occurrence of an inconvenience when the value indicative of the amount of change of the gap d measured by the displacement sensor 17 exceeds a predetermined threshold value.

Figure 13:
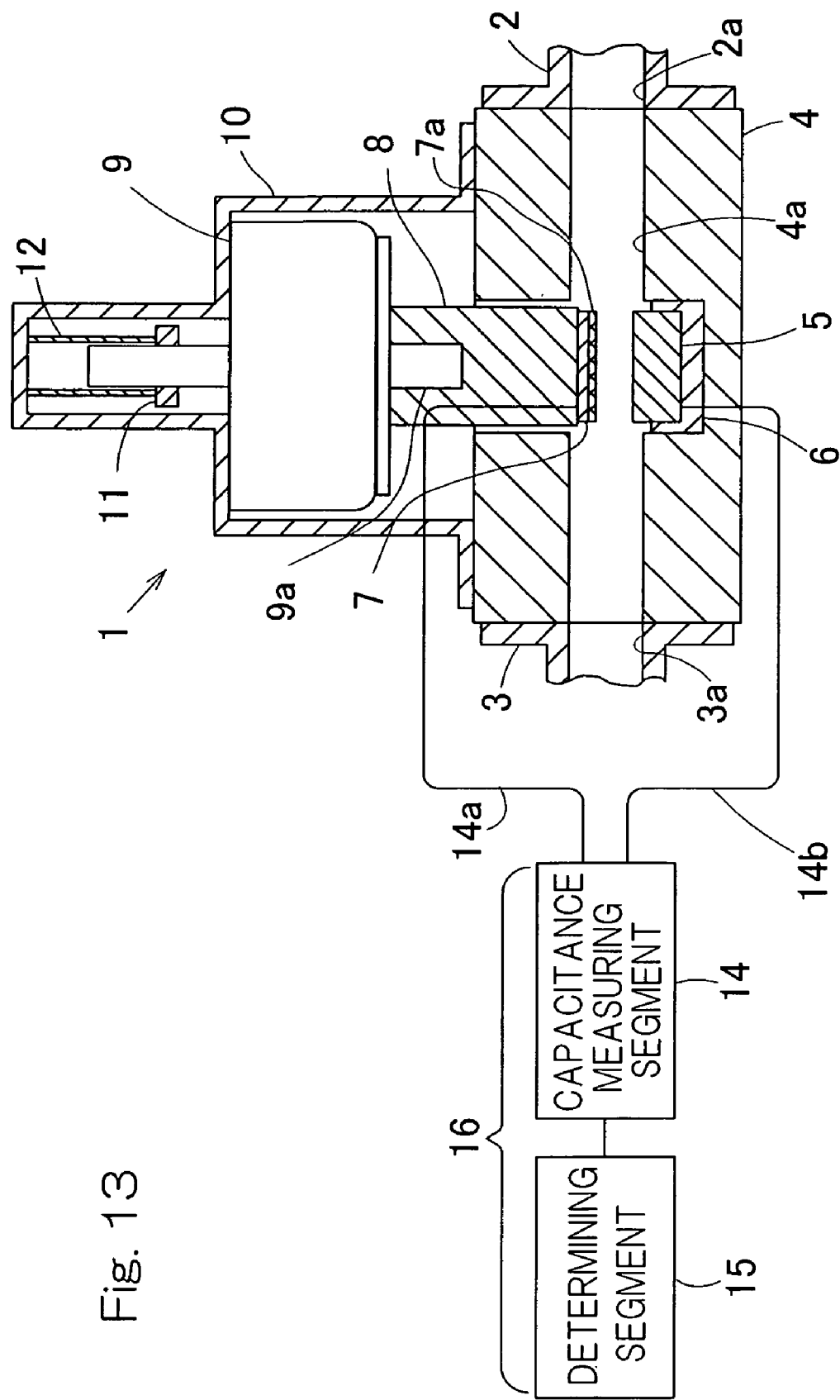
Figure 14:
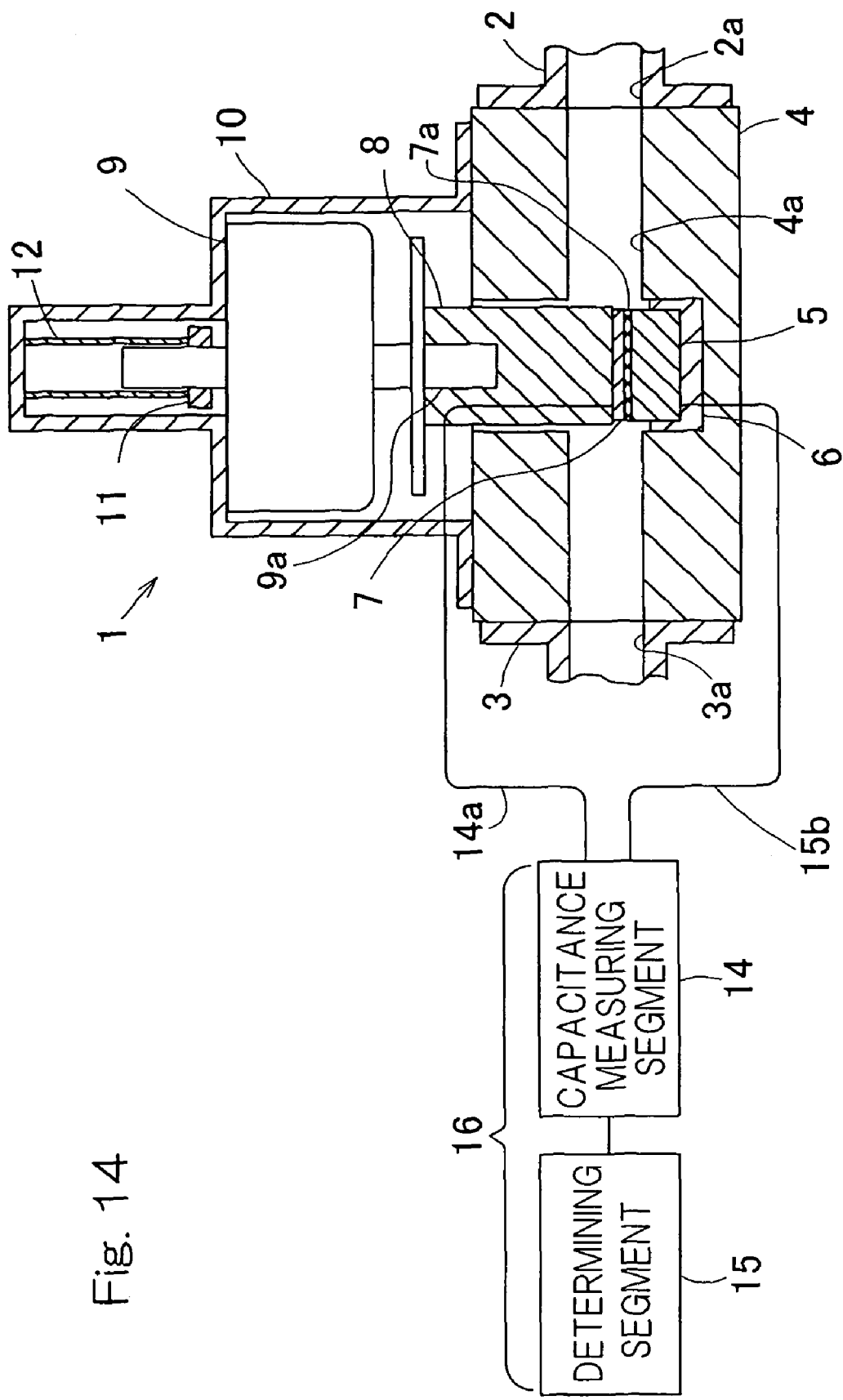
FIG. 14 is a schematic structural diagram showing the broken piece detecting sensor assembly according to the sixth preferred embodiment in a condition when the supply of an electric power is halted.

In the following description, the broken piece detecting sensor assembly according to a sixth preferred embodiment of the present invention will be described in detail with particular reference to FIGS. 13 to 16. FIG. 13, corresponding to FIG. 1 for the first embodiment, is a schematic structural diagram showing the broken piece detecting sensor assembly according to the sixth embodiment in a condition in which the broken piece detecting sensor assembly is electrically powered on, and FIG. 14, similarly corresponding to FIG. 2 for the first embodiment, is a schematic structural diagram showing the broken piece detecting sensor in a condition in which the broken piece detecting sensor assembly is not electrically powered on, in which like parts are designated by like reference numerals except that only difference will be described hereinafter. In the case of this sixth embodiment, an insulating layer 7a is provided on a surface of the movable flat plate 7 confronting the stationary flat plate 5. This insulating layer 7a preferably has a thickness within the range of a few micrometer to some tens micrometer and is made of a material having a high dielectric constant. By way of example, the movable flat plate 7 may be made of aluminum material and may have its surface alumite treated to provide the insulating layer 7a. Alternatively, the insulating layer 7a may be formed by spraying a ceramic material onto that surface of the movable flat plate 7. Yet, in place of the provision of the insulating layer 7a on the movable flat plate 7, a similar insulating layer may be provided on the stationary flat plate 5, or the insulating layer may be formed on respective surfaces of the two flat plates 5 and 7 that confront with each other.

Figure 15:
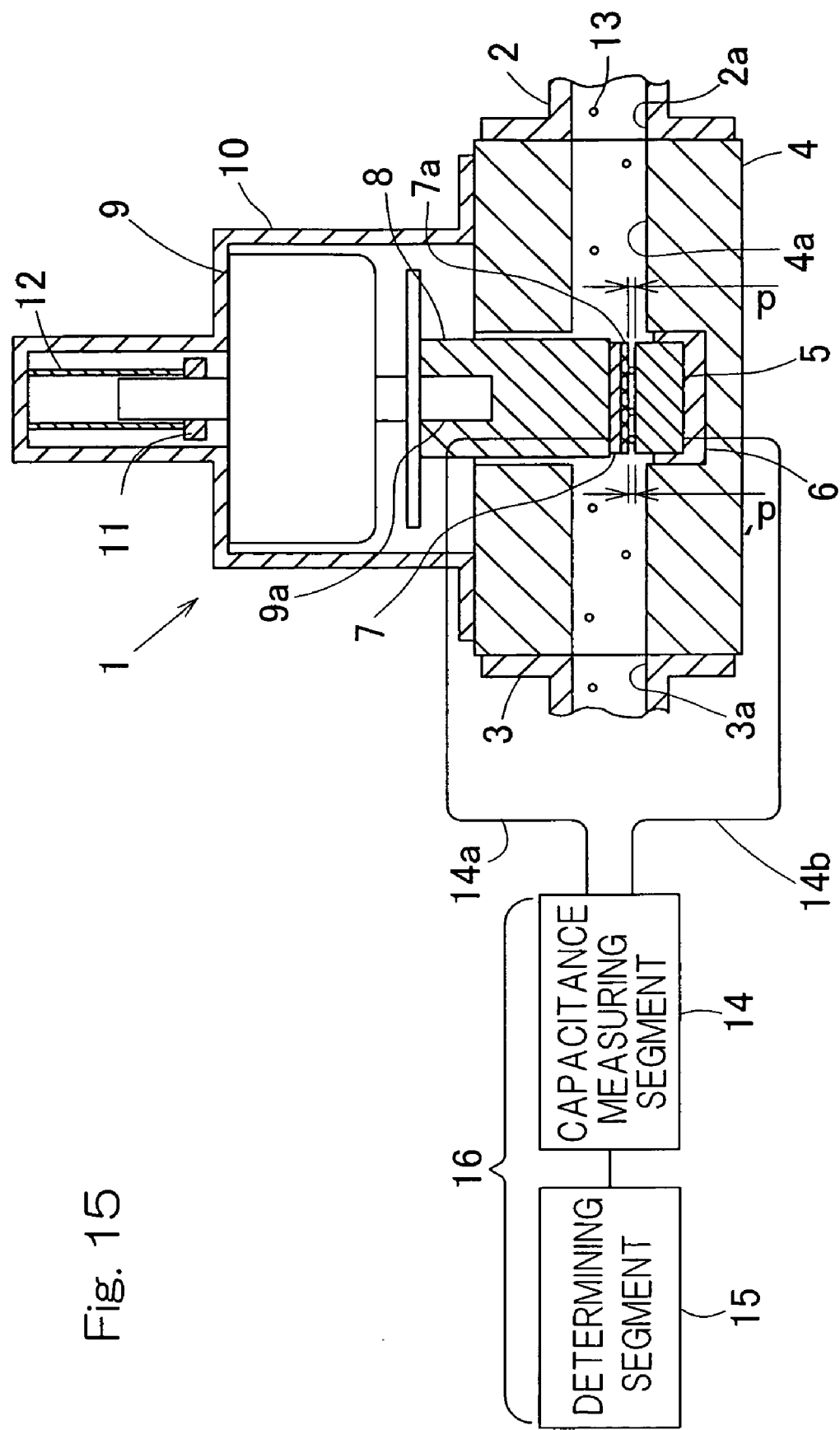
FIG. 15 is an explanatory diagram showing the detecting operation performed by the broken piece detecting sensor assembly according to the sixth preferred embodiment.

The detecting operation of the broken piece detecting sensor assembly according to this sixth embodiment to detect the broken piece contained in the lubricant oil takes place in a manner similar to that shown and described in connection with the first embodiment. Although the details thereof are not therefore reiterated for the sake of brevity, as best shown in FIG. 15, where the broken piece 13 of various materials resulting from frictional wear and/or breakage of an combustion engine, a gear box and/or bearing assemblies is admixed in the lubricant oil, such broken piece 13 is sandwiched between the movable flat plate 7 and the stationary flat plate 5. In such case, the gap d, corresponding to the thickness of the broken piece 13, and a gap d' corresponding to the thickness of the insulating layer 7a formed on the surface of the movable flat plate 7 are formed between the movable flat plate 7 and the stationary flat plate 5. Hence, the composite capacitance C attributable to the gap d and the gap d' is formed between the movable flat plate 7 and the stationary flat plate 5.

As hereinbefore discussed, the capacitance C between the parallel flat plates is generally known as having the following relationship.

$$C = \epsilon_o \cdot \epsilon_r \cdot S / d \qquad (3)$$

Also, the composite capacitance C of the two capacitances C1 and C2 connected in series with each other is generally known as expressed by the following equation.

$$C = (C1 \times C2)/(C1+C2) \qquad (4)$$

From the equation (3) above, it will readily be seen that the capacitance C1 [F] attributable to the gap d corresponding to the thickness of the broken piece 13 is represented by the product of the dielectric constant $\epsilon_o$ (=8.854×10$^{-12}$ [F/m]) in the vacuum times the dielectric constant Fr of the lubricant times the surface area S [m$^2$] of the parallel flat plates, which is then divided by the gap d [m] between the parallel flat plates. Similarly, the capacitance C2 [F] attributable to the gap d' corresponding to the thickness of the insulating layer 7a is represented by the product of the dielectric constant $\epsilon_o$ (=8.854×10$^{-12}$ [F/m]) in the vacuum times the dielectric constant $\epsilon_r$' of the insulating layer 7a times the surface area S [m$^2$] of the parallel flat plates, which is then divided by the gap d' [m] between the parallel flat plates.

In the case of this sixth embodiment, the respective dielectric constants $\epsilon_r$ and $\epsilon_r$' of the lubricant and the insulating layer 7a, the gap d' corresponding to the thickness of the insulating layer 7a and the surface area S of the parallel flat plates are constant, the composite capacitance C of the two capacitances C1 and C2 shown in the equation (4) depends on the gap d corresponding to the thickness of the broken piece 13. In view of this, when the composite capacitance C between the two flat plates 5 and 7 is measured by the capacitance measuring segment 14, the value of the gap d corresponding to the thickness of the broken piece 13 can be detected, from which the size of or the amount of the broken piece 13 accumulated can be estimated.

On the other hand, if no broken piece 13 is present between the two flat plates 5 and 7, the gap d of a very micro size is formed in the presence of the lubricant oil between those flat plates 5 and 7, or the flat plates 5 and 7 (the stationary flat plate 5 and the insulating layer 7a in the movable flat plate 7) are held in contact with each other. In the case of the gap d of the very micro size attributable to the lubricant oil, the capacitance C1 exhibits a considerably high value when compared with that exhibited by the presence of the broken piece 13 between the flat plates 5 and 7 and the composite capacitance C will be represented by the value of the capacitance C2 induced by the gap d' corresponding to the thickness of the insulating layer 7a. Since the value of the capacitance C2 is fixed, the size of change in gap can be estimated from a change in composite capacitance C induced by the broken piece 13.

In particular, since in this broken piece detecting sensor the insulating layer 7a is provided on the surface of at least one of the two flat plates 5 and 7, which faces the other of those two flat plates 5 and 7 (i.e., on the surface of the movable flat plate 7 in the illustrated instance), it is possible to assuredly estimate the gap d corresponding to the thickness of the broken piece 13 by converting it into the capacitance, even though the broken piece 13 to be sandwiched between the two flat plates 5 and 7 is made up of broken remains of electroconductive material. In other words, assuming that even in this sixth embodiment, no insulating layer 7a is formed in the movable flat plate 7, sandwiching of the broken piece 13, made up of the broken remains of electroconductive material, between the two flat plates 5 and 7 may result in establishment of an electric circuit between those two flat plates 5 and 7 despite the presence of a gap corresponding to the thickness of the broken piece 13, hence resulting in incapability of measuring the gap. However, the provision of the insulating layer 7a in, for example, the movable flat plate 7 as described above is effective to prevent such an inconvenience from occurring in measurement. The capacitance measuring segment 14 may be employed in the form of a measuring instrument such as, for example, an electric capacitance meter.

Figure 16:
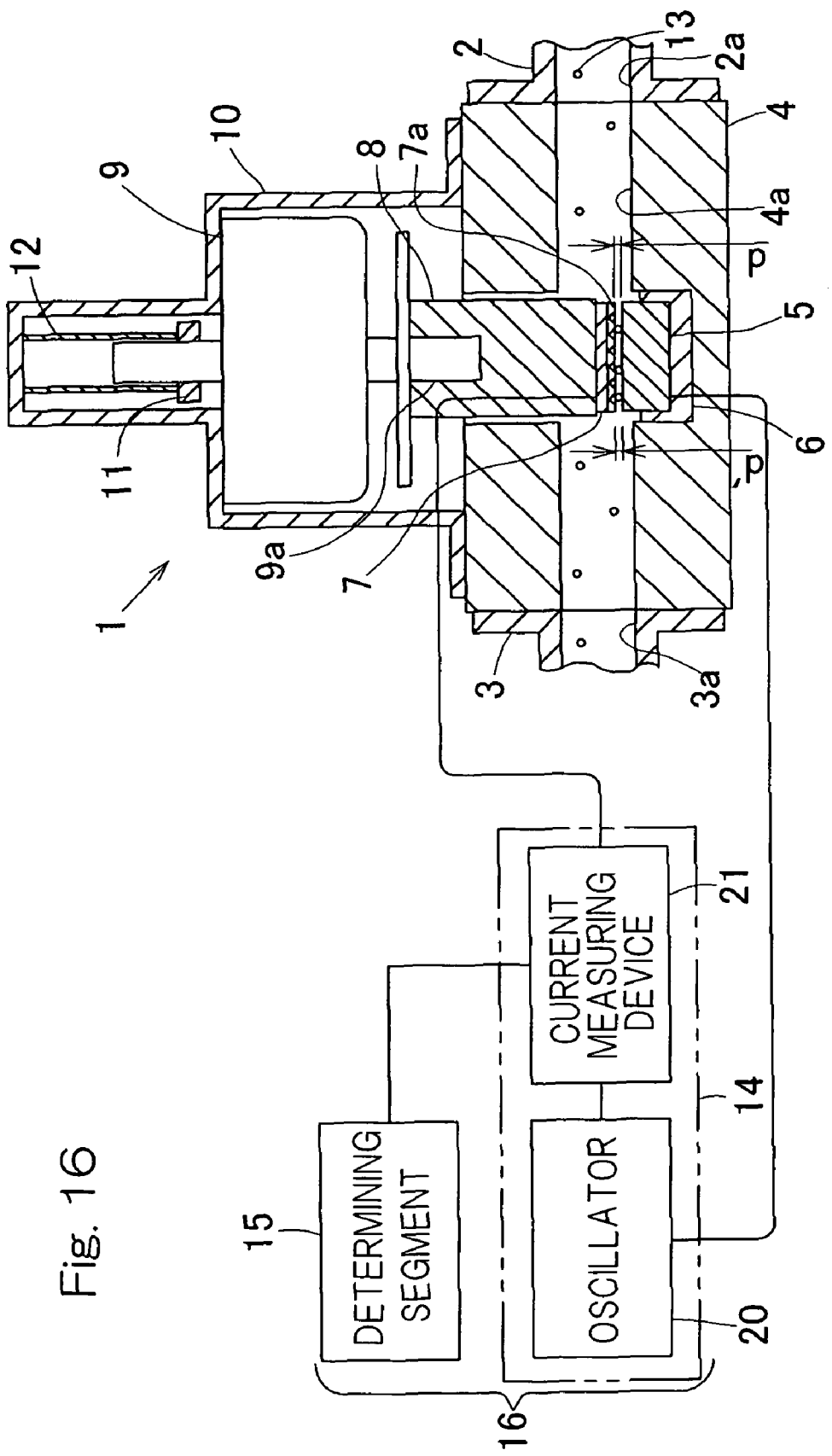
FIG. 16 is an explanatory diagram showing the detecting operation which takes place when one constructional example of the capacitance measuring segment is utilized in the broken piece detecting sensor assembly according to the sixth preferred embodiment.

FIG. 16 illustrates an example of the structure of the capacitance measuring segment 14 which forms a part of the measuring and determining section 16 employed in the broken piece detecting sensor assembly shown in and described with reference to FIG. 13. This capacitance measuring segment 14 is made up of a series connected circuit of an oscillator 20 and a current measuring device 21 in a manner similar to that shown in and described with reference to FIG. 4 and is so designed and so configured that the oscillator 20 may supply an alternating current to the movable flat plate 7 and the stationary flat plate 5 and the current measuring device 21 may measure the capacitance C between the flat plates 5 and 7 in terms of the impedance. In this case, the capacitance C can be determined from the impedance so measured. Other structural features than those described above are similar to those shown in and described with reference to FIG. 13.

The capacitance measuring segment 14 that may be employed in the practice of the sixth embodiment of the present invention may not be always limited to the one shown in and described with reference to FIG. 16, but may be the one shown in the circuit diagram of FIG. 5 as the second embodiment of the present invention or the one shown in the circuit diagram of FIG. 6 as the third embodiment of the present invention.

Figure 17:
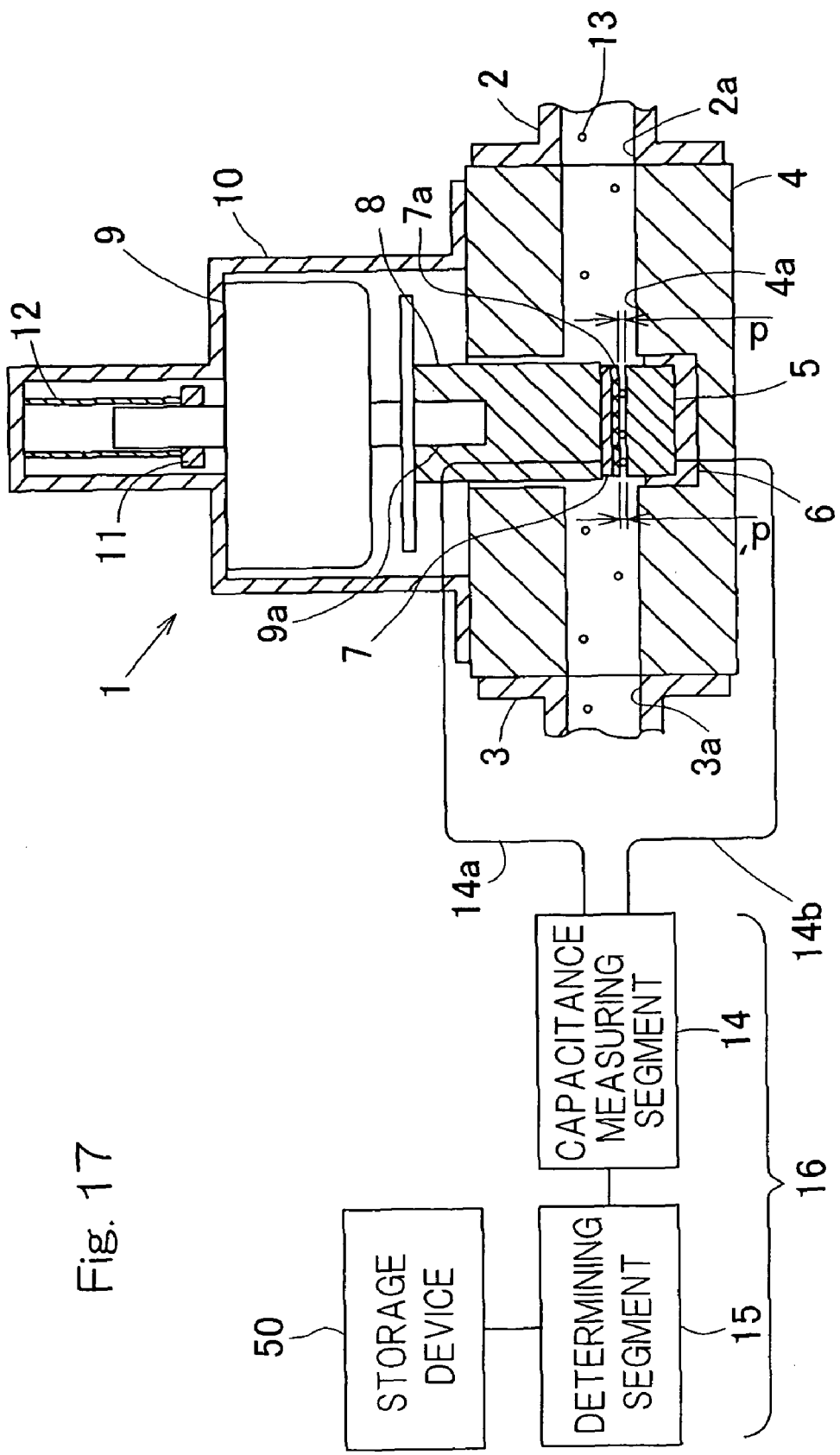

FIG. 17 illustrates a seventh preferred embodiment of the broken piece detecting sensor assembly according to the present invention. This seventh embodiment is similar to the sixth embodiment shown in and described with reference to FIG. 13, except that in accordance with the seventh embodiment, a storage device 50 is added to the stage next to the determining segment 15 so that the status of the broken piece 13 admixed in the lubricant oil can be monitored in real time. The capacitance measuring segment 14 may be identical with that shown in and described with reference to any one of FIGS. 5, 6 and 16. It is to be noted that the determining segment 15 may be of a type capable of determining the occurrence of an inconvenience when the extent to which the capacitance measured by the capacitance measuring segment 14 changes exceeds a predetermined threshold value.

Figure 18:
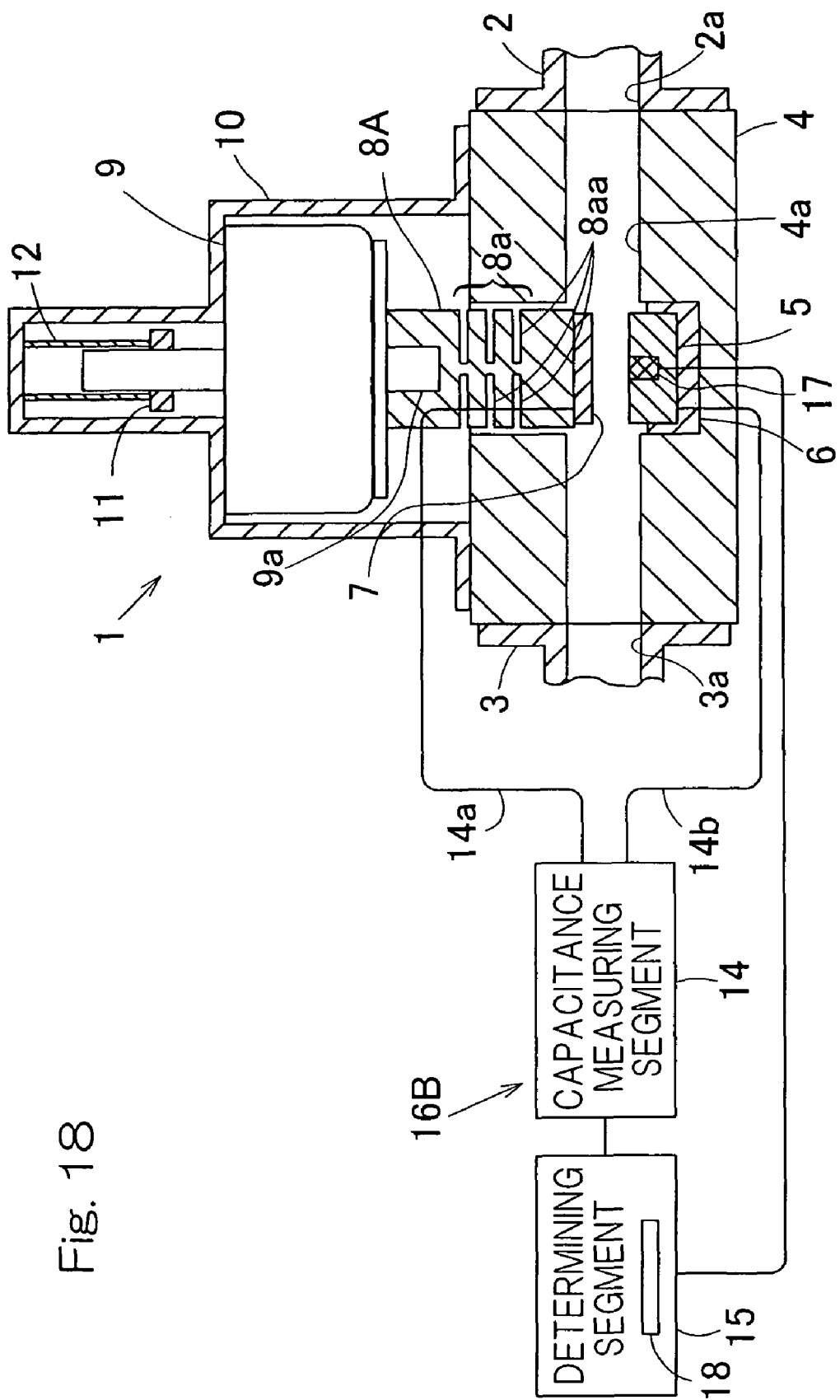
Figure 19:
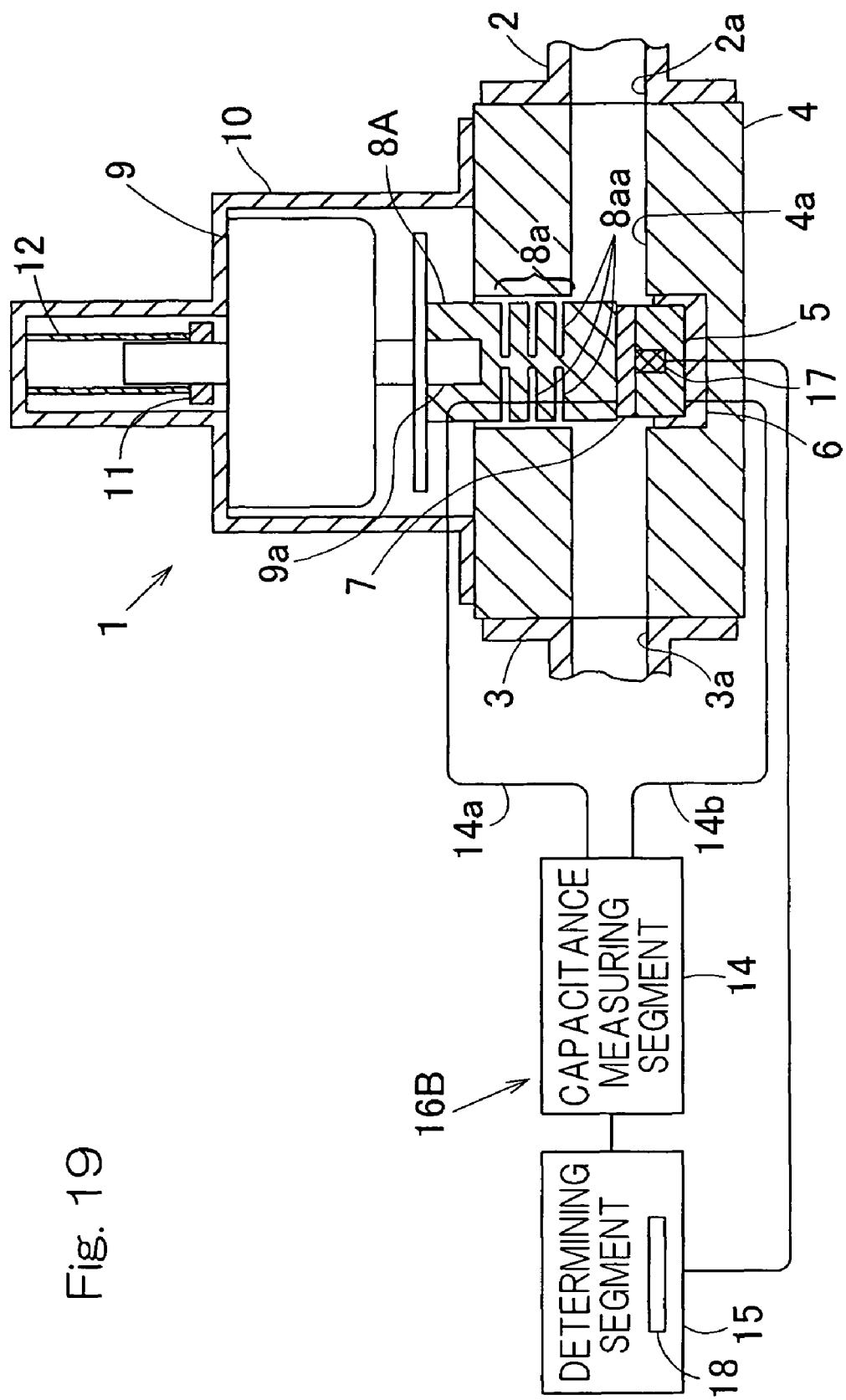
FIG. 19 is a schematic structural diagram showing the broken piece detecting sensor assembly according to the eighth preferred embodiment in a condition when the supply of an electric power is halted.
Figure 20:
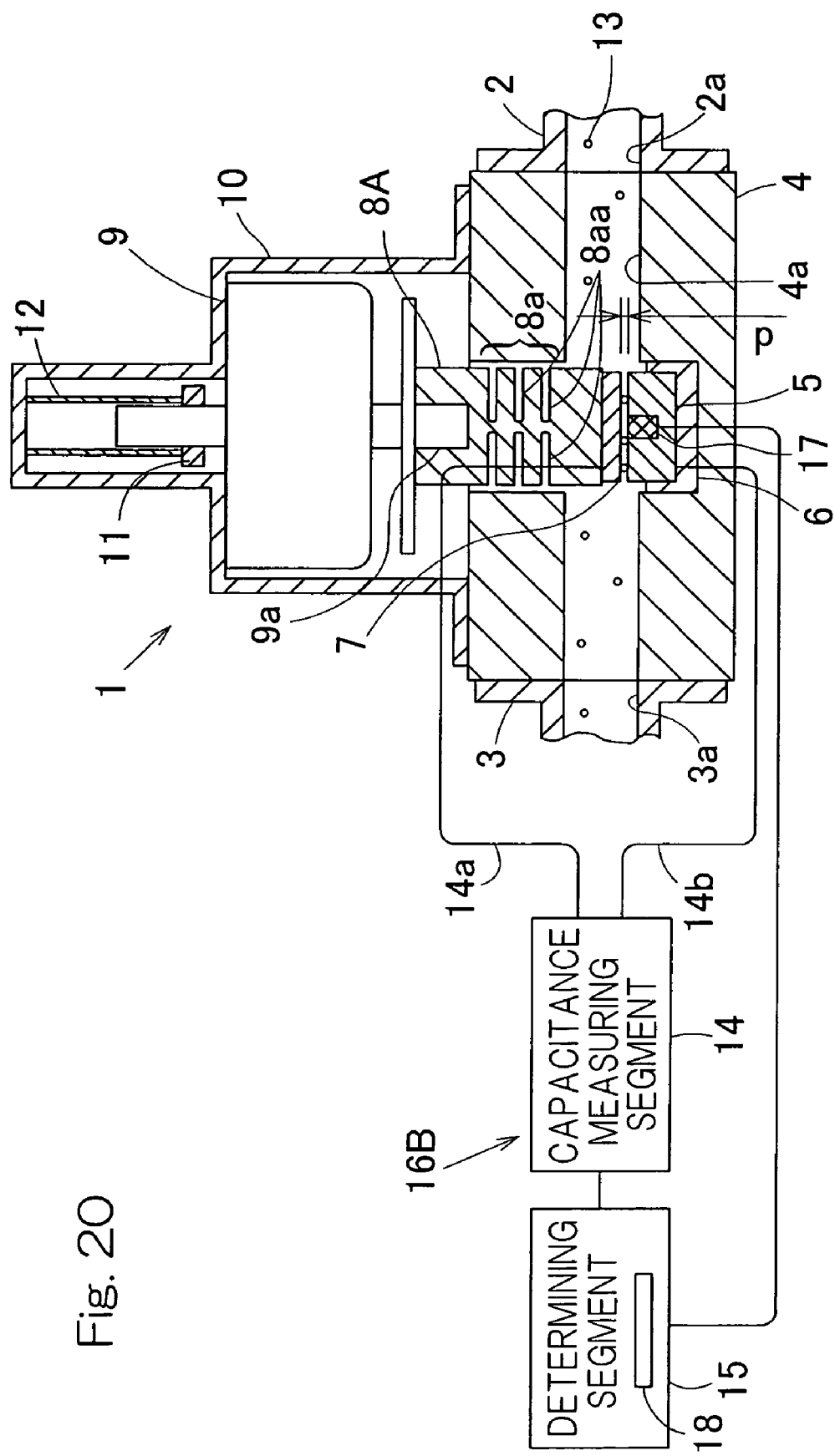
FIG. 20 is an explanatory diagram showing the detecting operation performed by the broken piece detecting sensor assembly according to the eighth preferred embodiment.

An eighth preferred embodiment of the present invention will be hereinafter described with particular reference to FIGS. 18 to 21. FIG. 18 is a schematic structural diagram showing the broken piece detecting sensor assembly according to a tenth preferred embodiment of the present invention in a condition in which the broken piece detecting sensor assembly is electrically powered on, and FIG. 19 is a schematic structural diagram showing the broken piece detecting sensor in a condition in which the broken piece detecting sensor assembly is not electrically powered on. Like parts similar to those shown in connection with the first embodiment are designated by like reference numerals and the details thereof are not therefore reiterated for the sake of brevity, noting that only differences will be described.

As shown in FIG. 18, in this eighth embodiment, in place of the fixing member 8 shown in FIG. 1 and described in connection with the first embodiment, a flexible support member 8A is employed, which is a support member made of an insulating material and having a flexibility.

The flexible support member 8A referred to above is a rod-like member protruding from the free end of the movable shaft 9a in a direction towards the stationary flat plate 5 and having a flexibility, with the movable flat plate 7 secured to a free end thereof. In the instance as shown, the flexible support member 8A has a generally intermediate portion which is defined as a coupling member 8a for providing the freedom of tilting direction of the movable flat plate 7. For a base material of the flexible support member 8A, for example, an aluminum material capable of maintaining a rigidity even at elevated temperatures, which is surface treated with an alumite treatment, is employed. The coupling member 8a referred to above is defined by forming, in that generally intermediate portion of the base material for the flexible support member 8A, a plurality of cuts each in the form of a circumferentially extending groove and cut radially inwardly in a direction perpendicular to the longitudinal axis of the flexible support member 8A. The flexible support member 8A may not be always limited to that shown and described, but may be in the form of a composite body including a base body, made of a rigid material, and an elastic member such as, for example, a heat resistant rubber sandwiched between a free end of the base body and the movable flat plate 7.

The measuring and determining section 16B is made up of the capacitance measuring segment 14, the displacement sensor 17 and the determining segment 15. The capacitance measuring segment 14 is employed in the form of a measuring device that utilizes electrodes, having an electrode 14a, connected with the movable flat plate 7, and an electrode 14b connected with the stationary flat plate 5 and operable to measure the capacitance between the movable flat plate 7 and the stationary flat plate 5. The displacement sensor 17 is a gap sensor for measuring the gap between the movable flat plate 7 and the stationary flat plate 5 and is, for example, disposed having been embedded in the stationary flat plate 5. In the instance now under discussion, an eddy current type is employed for the displacement sensor 17, but any other type such as, for example, a magnetic type or an optical type may be employed therefor. The determining segment 15 estimates the presence of absence of the broken piece 13 (FIG. 20) admixed in the lubricant oil, the kind of material of the broken piece 13, the size thereof or the amount of the broken piece 13 accumulated in reference to the measured values given respectively by the capacitance measuring segment 14 and the displacement sensor 17 and includes a determining rule in the form of, for example, a table or a calculating equation defining the relationship between the measured value and the result of determination so that by comparing the measured value with the determining rule, a result of determination can be outputted therefrom. The determining segment 15 also includes an electroconductive material detector 18 for determining the detection of an electroconductive material as a portion of its functionality.

The details of the detecting operation accomplished by the broken piece detecting sensor assembly according to the eighth embodiment described above will not be reiterated for the shake of brevity since it is performed in a manner similar to that performed by the broken piece detecting sensor assembly according to the first embodiment.

During the broken piece detecting operation performed by the broken piece detecting sensor assembly according to the eighth embodiment, when the broken piece 13 sandwiched between the stationary flat plate 5 and the movable flat plate 7 is made of an electroconductive material, the two electrodes 14a and 14b is short-circuited with each other and, therefore, the gap d2 determined from the measurement of the capacitance C and with the use of the equation (3) above will represent zero or an extremely small value. In contrast thereto, the gap d1 obtained by the displacement sensor 17 will represent a value different from that given by the gap d2 that is estimated from the measured value of the capacitance measuring segment 14. Thus, by detecting the difference between those two results of measurement, it is possible to determine whether the broken piece 13 so detected is electroconductive or non-electroconductive. More specifically, the electroconductive material detector 18 of the determining segment 15 has a function of determining the detection of the broken piece made up of the broken remains of electroconductive material and if the following relation establishes;

$$d1 \gg d2 \quad (5)$$

it determines that the broken piece 13 detected is made up of the broken remains of electroconductive material. Also, in the event that those two values d1 and d2 represent respective values are close to each other, but do not represent a zero gap, that is, in the event that the following relation establishes;

$$d1 \approx d2 (\neq 0) \quad (6)$$

it determines that the broken piece 13 detected is made up of the broken remains of non-electroconductive material. Yet, the determining segment 15 outputs the size of the broken piece 13 in the form represented by the detected value d1 of the displacement sensor 17.

On the other hand, even when no broken piece 13 is present between the two flat plates 5 and 7, the two electrodes 14a and 14b are short-circuited with each other and, therefore, the gap d determined from the measurement of the capacitance C will represent zero or a very small value. In such case, the gap d1 measured by the displacement sensor 17 also represents zero, and accordingly the determining segment 15, based on those results of measurement, concludes that no broken piece 13 is present between the two flat plates 5 and 7.

In the foregoing description, the stationary flat plate 5 and the movable flat plate 7 have been shown and described as operable to sandwich the broken piece 13 therebetween while they assumes a condition of parallel flat plates. In practice, however, it is quite often that broken piece 13 made up of a multiplicity of finely divided particles of varying sizes is sandwiched and, therefore, the stationary flat plate 5 and the movable flat plate 7 sandwich such broken piece therebetween while they assume a condition of non-parallel flat plates. Since the movable flat plate 7 is fixedly supported by the movable shaft 9a of the shift mechanism 9 through the flexible support member 8A as hereinbefore described, the movable flat plate 7 can be at this time brought into contact with the broken piece 13 in a manner tilted relative to the stationary flat plate 5 by the effect of the flexibility or elasticity of the coupling member 8a (or elastic member) of the flexible support member 8A. In addition, since the constant preload is applied from the compression spring 12 to the movable flat plate 7 as hereinbefore described, the movable flat plate 7 can be urged to assume the most stable tilted attitude relative to the stationary flat plate 5 and, therefore, the gap proportional to the size of the broken piece 13 then sandwiched can be secured. In view of the foregoing, in place of the movable flat plate 7, the stationary flat plate 5 may be supported to the base member 4 through the flexible support member 8A.

At this time, however, the capacitance measured by the capacitance measuring segment 14 will be different from the capacitance measured during the condition of completely parallel flat plates and the value d2 of the gap estimated from the capacitance will not coincide with the actual size of the broken piece 13. Even so, it does not affect so much in detecting the status of the broken piece 13 since the gap will become large, when large broken piece 13 is sandwiched, and the trend of the capacitance proportional to the size of the broken piece 13 can be obtained.

Figure 21:
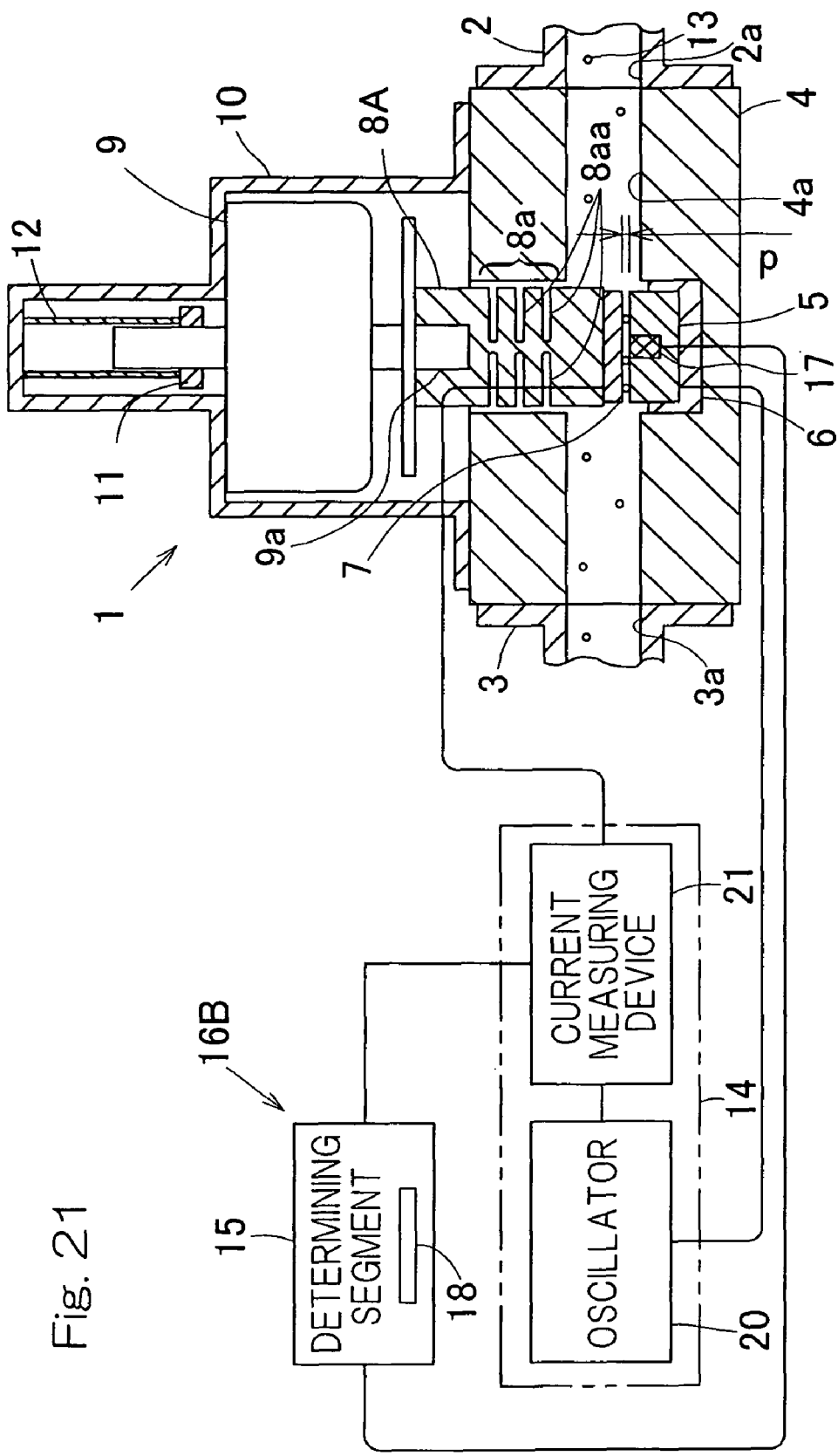
FIG. 21 is an explanatory diagram showing the detecting operation which takes place when a constructional example of a capacitance measuring segment is utilized in the broken piece detecting sensor assembly according to the eighth preferred embodiment.

FIG. 21 illustrates an example of the structure of the capacitance measuring segment 14 which forms a part of the measuring and determining section 16B employed in the broken piece detecting sensor assembly shown in FIG. 18. This capacitance measuring segment 14 includes an oscillator 20 and a current measuring device 21 connected in series with the oscillator 20 and is so designed and so configured that the oscillator 20 may supply an alternating current to the movable flat plate 7 and the stationary flat plate 5 and the current measuring device 21 may measure the capacitance C between the flat plates 5 and 7 in terms of the impedance. In this case, the capacitance C can be determined from the impedance so measured. Other structural features than those described above are similar to those shown in and described with reference to FIG. 18. Also, the capacitance measuring segment 14 of the circuit configuration shown in and previously described with reference to any one of FIGS. 5 and 6 may be replaced with the capacitance measuring segment 14 shown in and described with reference to FIG. 21.

As hereinabove described, since the broken piece detecting sensor assembly according to the eighth embodiment of the present invention is so designed and so configured that the movable flat plate 7 can be driven to sandwich the broken piece 13 between it and the stationary flat plate 5 to thereby allow the measuring and determining section 16B to measure the gap between those two flat plates 7 and 5 so that the presence or absence of the broken piece 13, the size of the broken piece 13 or the amount of the broken piece 13 accumulated can be determined and, on the other hand, since the movable flat plate 7 is fixedly supported by the flexible support member 8A, the movable flat plate 7 can be brought into contact with the broken piece 13 in an attitude stabilized and tilted by the effect of the flexibility or elasticity of the flexible support member 8A, even though a multiplicity of pieces of broken piece 13 of varying sizes, for example, are held in a condition sandwiched between those two flat plates 5 and 7. Accordingly, the measured value given by the measuring and determining section 16B can be stabilized and the presence or absence of, the size of or the amount of the broken piece 13 accumulated can be stably detected.

Also, the eighth embodiment of the present invention is so designed and so configured that not only is the capacitance between the movable flat plate 7 and the stationary flat plate 5, which are utilized as respective electrodes, detected by the capacitance measuring segment 14, but the gap between those two flat plates 5 and 7 is also measured by the displacement sensor 17, so that not only the presence or absence of the broken piece 13 but also the material and the size of the broken piece 13 can be estimated from respective outputs of those two sensors 14 and 17. Therefore, the broken piece 13 made up of the various materials and admixed in the lubricant oil can be detected and the size thereof can also be detected along with identification of whether the detected broken piece 13 is made up of the broken remains of electroconductive material such as, for example, metallic material, or non-electroconductive material such as, for example, resin or ceramics.

It is to be noted that measuring the gap between the two flat plates 5 and 7 may not be always conducted by the combination of the capacitance measuring segment 14 and the displacement sensor 17, such as employed in the previously described embodiment, but may be conducted solely by the capacitance measuring segment 14 or solely by the displacement sensor 17.

In addition, although in describing the eighth embodiment of the present invention, the movable flat plate 7 has been shown and described as fixedly supported by the flexible support member 8A, the stationary flat plate 5 may be fixedly supported by a flexible support member in a manner similar to that applied to the movable flat plate 7. By way of example, the stationary flat plate 5 may be fixedly supported to the base member 4 through an elastic member such as, for example, a heat resistant rubber or through a spacer made of an insulating material and having a spring mechanism incorporated therein, so that the stationary flat plate 5 can assume a stable tilted attitude depending on the status of the broken piece 13 to be sandwiched.

Figure 22:
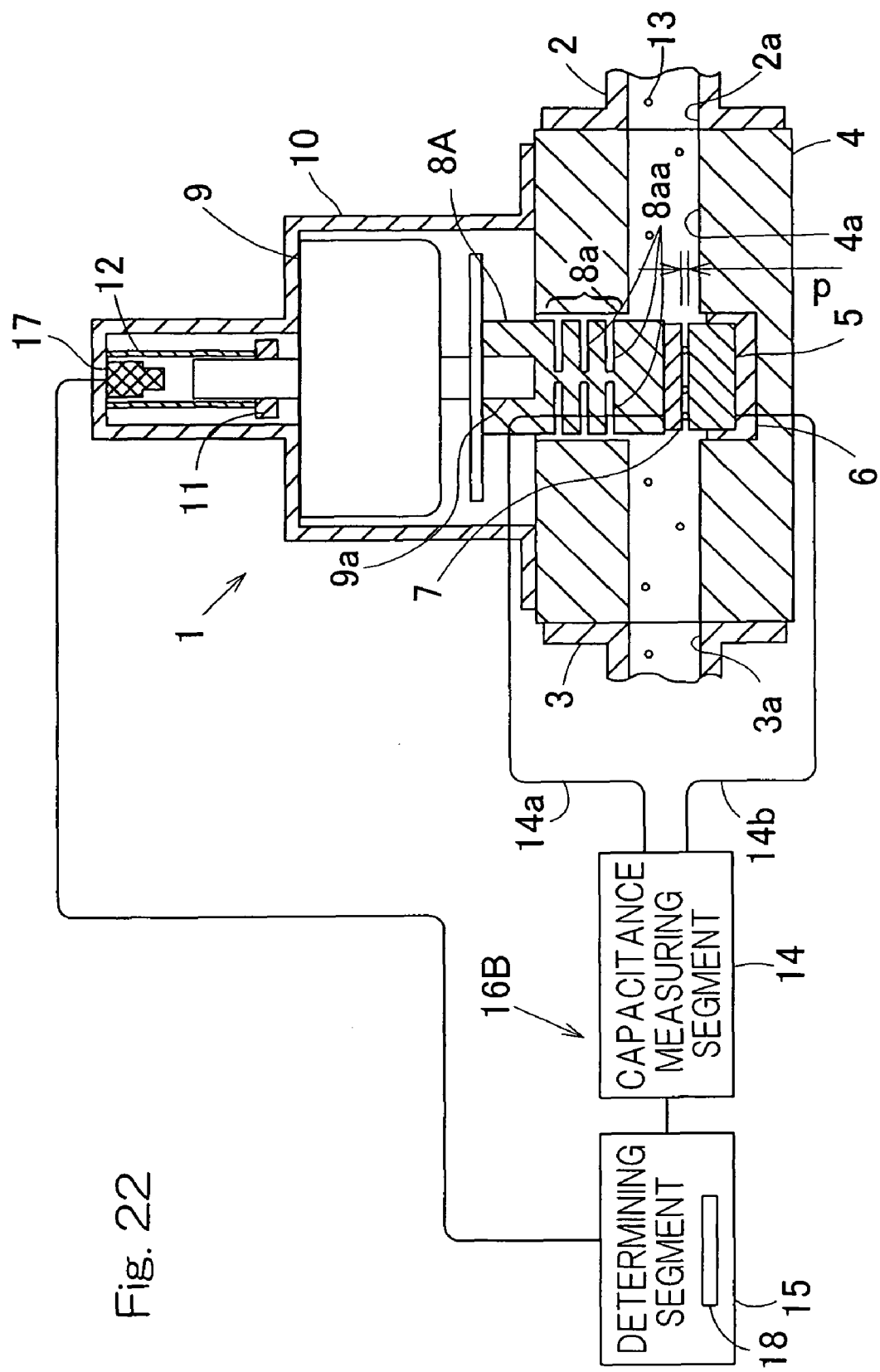
FIG. 22 is an explanatory diagram showing the detecting operation performed by the broken piece detecting sensor assembly according to a ninth preferred embodiment of the present invention.

FIG. 22 illustrates a ninth preferred embodiment of the present invention. This ninth embodiment is similar to the eighth embodiment shown in and described with particular reference to FIG. 18, but differs therefrom in that the displacement sensor 17 employed in the practice of the eighth embodiment is disposed within the actuator fixing member 10 at a position confronting the rear end of the movable shaft 9a.

In the case of this ninth embodiment, the displacement sensor 17 measures the amount of displacement of the movable shaft 9a, but since the movable flat plate 7 is fixed to the movable shaft 9a through the flexible support member 8A, the gap d between the stationary flat plate 5 and the movable flat plate 7 can be detected from the amount of displacement of the movable shaft 9a.

Figure 23:
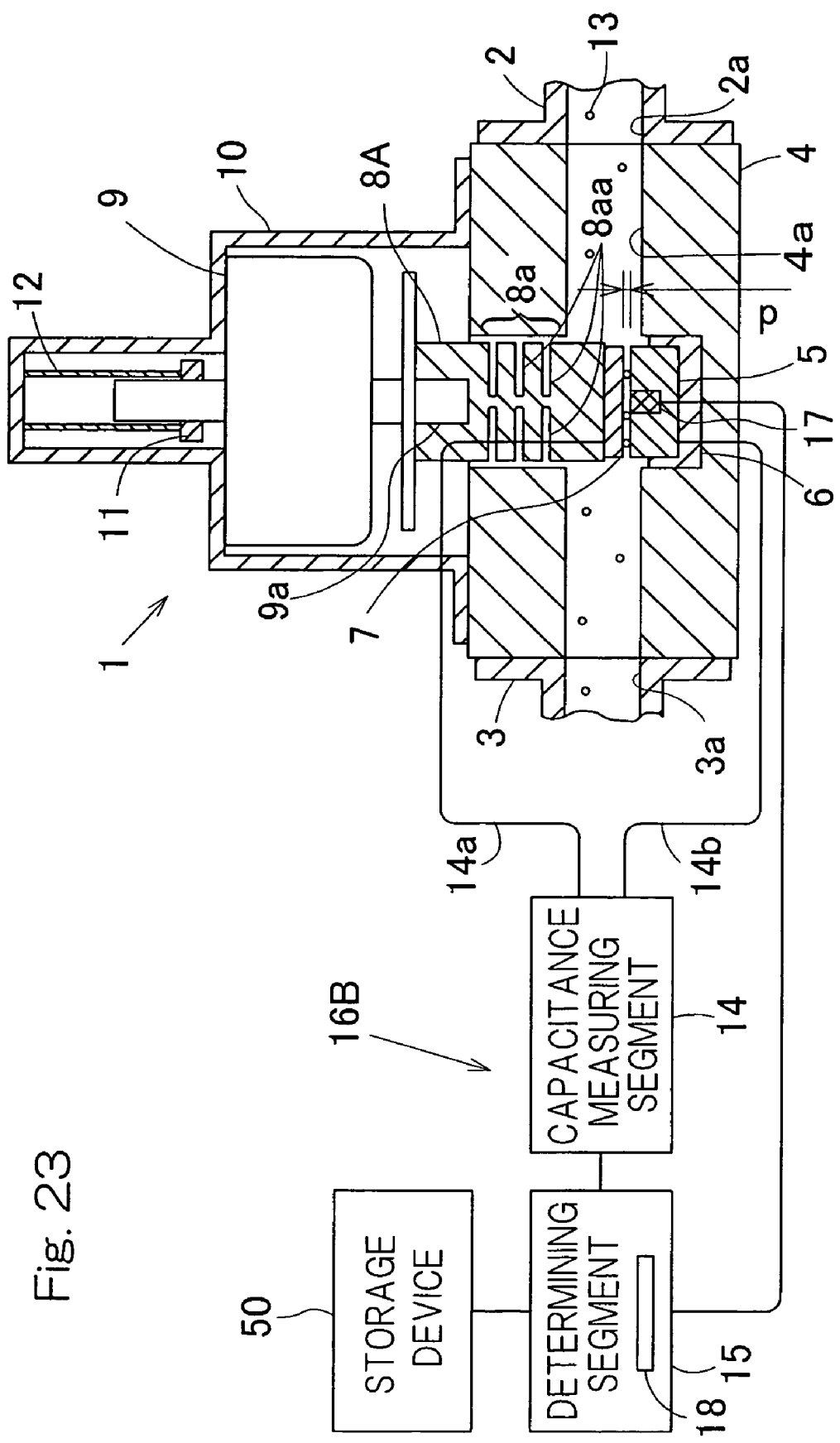
FIG. 23 is an explanatory diagram showing the detecting operation performed by the broken piece detecting sensor assembly according to a tenth preferred embodiment of the present invention.

FIG. 23 illustrates a tenth preferred embodiment of the present invention. This tenth embodiment is similar to the eighth embodiment shown in and described with particular reference to FIG. 18, but differs therefrom in that a storage device 50 is added to the stage next to the determining segment 15 so that the status of the broken piece 13 admixed in the lubricant oil can be monitored in real time. In this embodiment, the status of the lubricant oil can be inferred from the history of change of numerical values recorded and information on, for example, the tendency of increase of dirt and/or broken piece can be outputted. The capacitance measuring segment 14 may be of a circuit configuration shown in and described with any one of FIGS. 4, 5 and 21.

Figure 24:
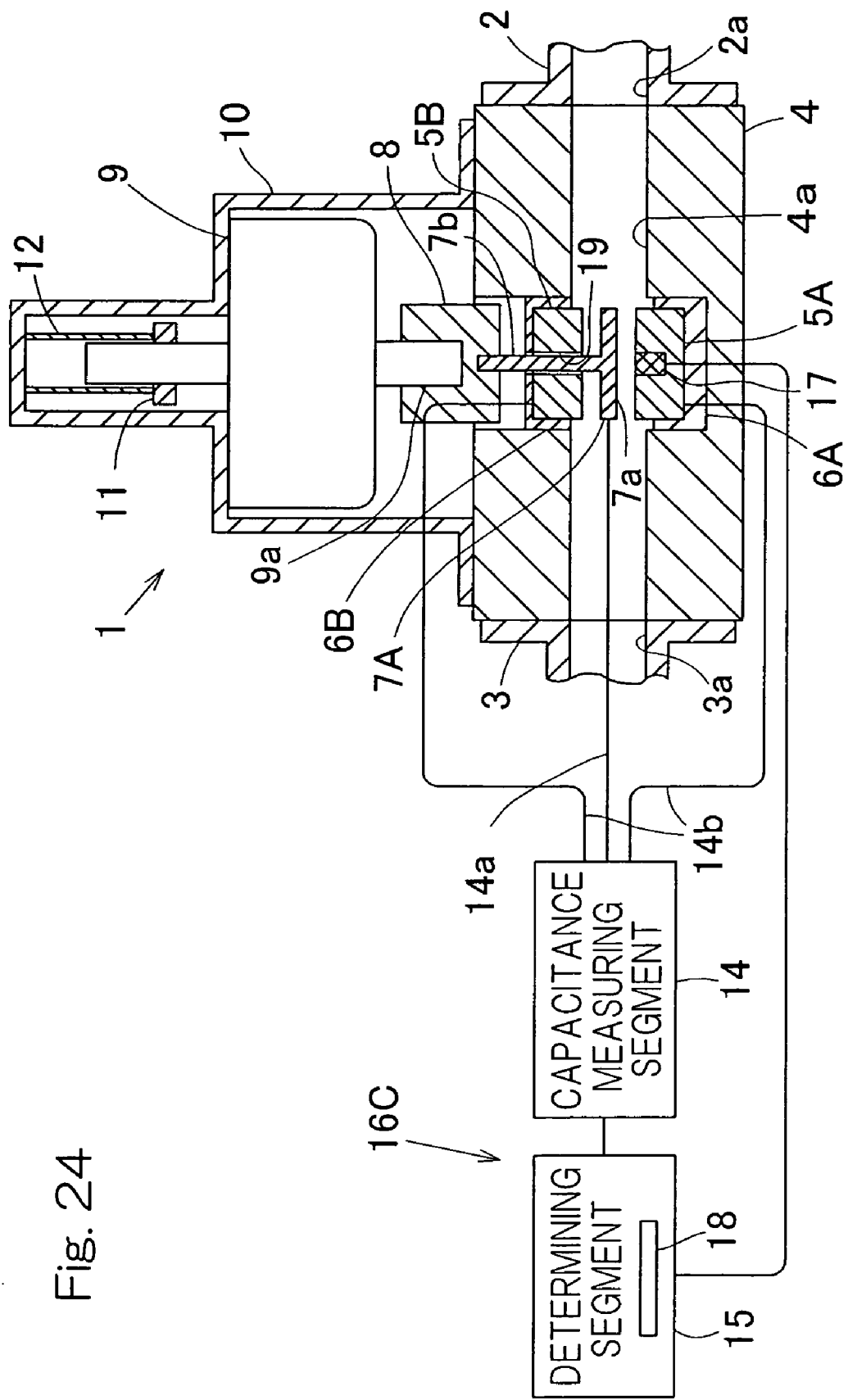

Hereinafter, an eleventh preferred embodiment of the present invention will be described in detail with particular reference to FIGS. 24 to 29. FIG. 24 illustrates a schematic structural diagram of the broken piece detecting sensor assembly according to this eleventh embodiment, in which component parts similar to those employed in the first embodiments are designated by reference numerals used therein and the details thereof are not reiterated for the sake of brevity. The broken piece detecting sensor assembly shown therein is a sensor for detecting broken piece admixed in a fluid forming an object to be examined and includes three electrodes 5A, 5B and 7A, a shift mechanism 9 for driving at least one of those three electrodes 5A, 5B and 7A to sandwich broken piece 13 (FIG. 27) between two of those electrodes, and a measuring and determining section 16C for measuring the gap between the two electrodes used to sandwich the broken piece 13 therebetween and then outputting one of the presence or absence of the broken piece 13, the size thereof or the amount of the broken piece 13 accumulated. In the case of this broken piece detecting sensor assembly, the lubricant oil is rendered to be the fluid forming the object to be examined.

Those three electrodes 5A, 5B and 7A and the shift mechanism 9 are incorporated in a sensor unit 1.

Those three electrodes 5A, 5B and 7A are all made of an electroconductive material and are arranged parallel to each other in a direction perpendicular to the direction in which the oil flow path 4a in the base member 4 extends within the base member 4, having been positioned generally intermediate of the oil flow path 4a. Of them, the electrode 5A is a stationary electrode in the form of a flat plate and fixed to the base member 4 in electrically insulated relation thereto through an electrode fixing member 6A made of an insulating material. This stationary electrode 5A is arranged on a lower side of the base member 4 with its surface oriented towards the oil flow path 4a. Another one of the electrodes, that is, the electrode 5B is a stationary electrode in the form of a flat plate and fixed to the base member 4 in electrically insulated relation thereto through another fixing member 6B made of an insulating material. This stationary electrode 5B is arranged on an upper side of the base member 4 with its surface confronting the oil flow path 4a and also confronting the stationary electrode 5A positioned therebelow. The remaining electrode 7A is a movable electrode of a T-sectioned configuration including an electrode base 7a of a flat plate shape and an insert body 7b extending from one surface of this electrode base 7a in direction at right angles thereto through a hole 19, defined in part in the stationary electrode 5B and in part in a fixing member 6B and is connected at a rear end of the insert body 7b with the movable shaft 9a of the shift mechanism 9 for reciprocating movement together with the movable shaft 9a. This movable electrode 7 is arranged with its electrode base 7a positioned intermediate between the stationary electrodes 5A and 5B within the oil flow path 4a such that opposite surfaces of the electrode base 7a are held respectively in face-to-face relation with the stationary electrodes 5A and 5B. It is to be noted that the insert body 7b of the movable electrode 7 that extends through the upper stationary electrode 5B is maintained electrically insulated from the stationary electrode 5B. Only the insert body 7b may be made of an insulating material so that it can be electrically insulated from the stationary electrode 5B.

Even this shift mechanism 9 may be identical with that employed in the practice of the first embodiment of the present invention, and the movable shaft 9a thereof is secured to the base member 4 through an actuator fixing member 10 for reciprocating movement in a direction, in which the oil flow path 4a extends in the base member 4. A free end of the movable shaft 9a of the shift mechanism 9 has an insert body 7b of the movable electrode 7 fixed thereto in electrically insulated relation thereto through the fixing member 8 made of an insulating material.

Figure 25:
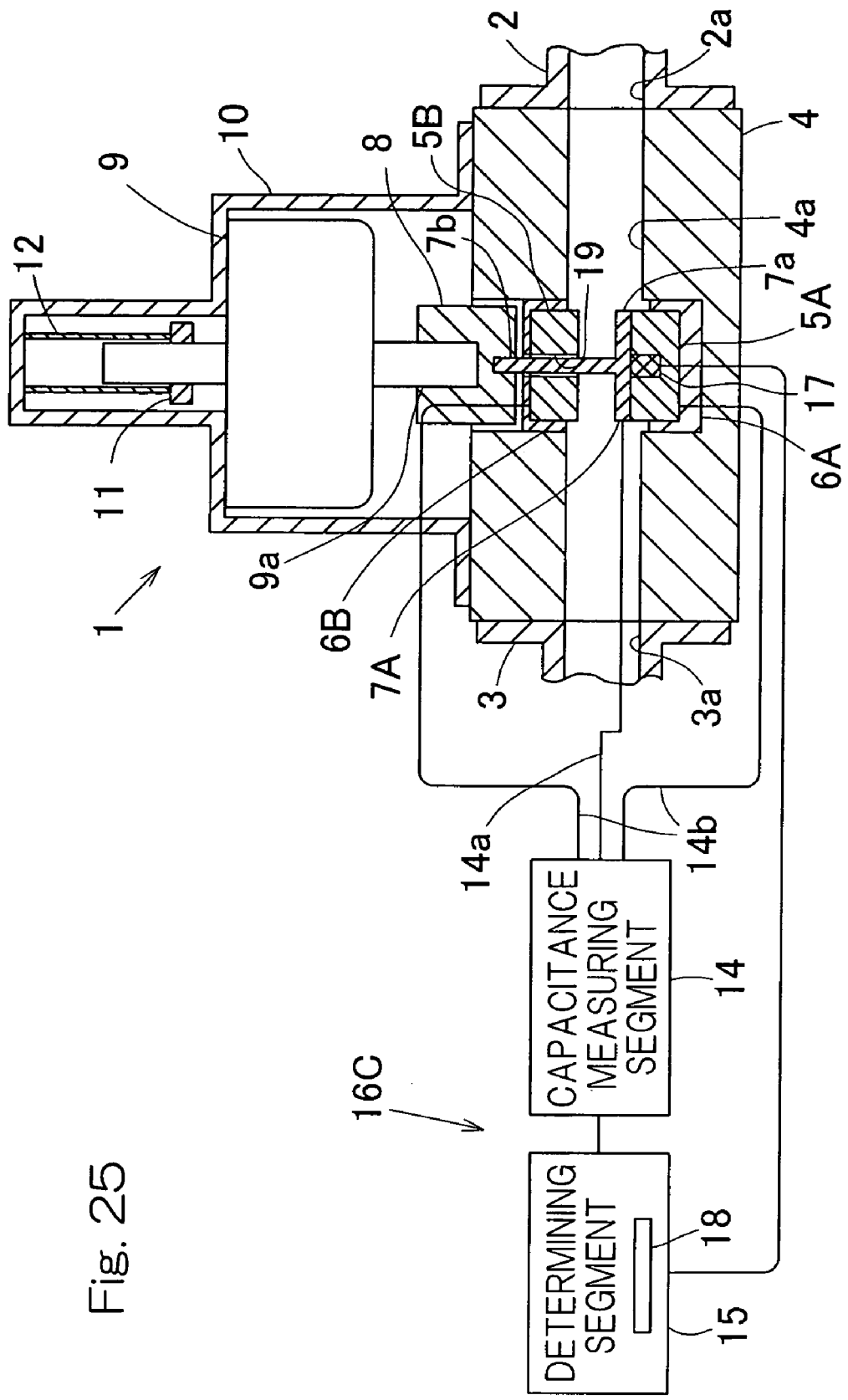
FIG. 25 is a schematic structural diagram showing the broken piece detecting sensor assembly according to the eleventh preferred embodiment operating under the first mode when the supply of an electric power is halted.
Figure 26:
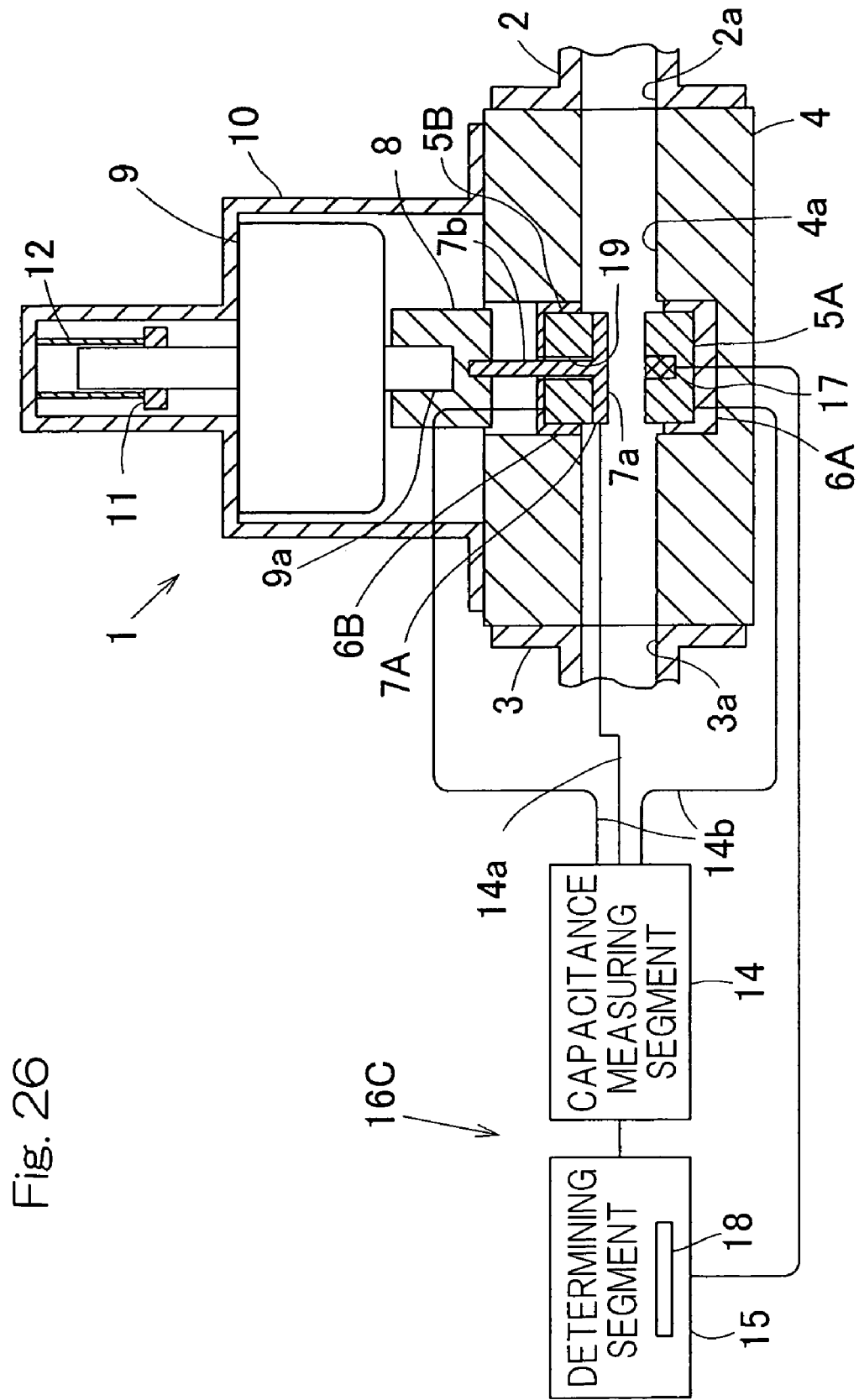

FIG. 24 illustrates a first mode, in which movement of the movable shaft 9 towards the advanced position is regulated with the shift mechanism 9 having been electrically powered on, in which condition the movable shaft 9a is somewhat retracted accompanied by axially inward compression of the compression spring 12 with the movable electrode 7A held at an intermediate position separated from both of the stationary electrodes 5A and 5B. On the other hand, in a condition in which the shift mechanism 9 has not yet been powered on electrically, the movable electrode 7A is advanced to contact the lower stationary electrode 5A, as shown in FIG. 25, by the effect of the resilient restoring force of the compression spring 12. Considering that the preload is applied from the compression spring 12 to the movable electrode 7A while the movable electrode 7A and the stationary electrode 5A are held in contact with each other, the movable electrode 7A and the stationary electrode 5A are in contact with each other under a predetermined pressure. FIG. 26 illustrates a second mode, in which with the shift mechanism 9 having been electrically powered on, the movable shaft 9a is retracted from the position, assumed during the first mode shown in FIG. 1, upwards towards the retracted position, in which condition the movable electrode 7A is held at a position where it contacts the upper stationary electrode 5B.

The measuring and determining section 16C includes a capacitance measuring segment 14, a displacement sensor 17 and a determining segment 15. The capacitance measuring segment 14 measures the capacitance between the movable electrode 7A and each of the stationary electrodes 5A and 5B, and has input terminals 14a and 14b connected respectively with the movable electrode 7A and both of the stationary electrodes 5A and 5B. The displacement sensor 17 is of the same type as that employed in the practice of the third embodiment, being a gap sensor for measuring the gap (distance) between the movable electrode 7A and each of the stationary electrodes 5A and 5B and is provided as embedded in, for example, the lower stationary electrode 5A. In this case, although the displacement sensor 17 serves to directly measure the gap between the movable electrode 7A and the lower stationary electrode 5A, the gap between the movable electrode 7A and the upper stationary electrode 5B is automatically calculated from the gap measured value between the movable electrode 7A and the lower stationary electrode 5A in view of the fact that the distance between the stationary electrodes 5A and 5B and the thickness of the electrode base 7a of the movable electrode 7A are constant.

The determining segment 15 includes a conduction or non-conduction determiner (electroconductive material detector) 18 having a part of its function to determine whether the broken piece 13 detected is an electroconductive material or a non-electroconductive material.

The broken piece detecting operation of the broken piece detecting sensor assembly according to this eleventh embodiment to detect the broken piece contained in the lubricant oil takes place in a manner similar to that shown and described in connection with the first embodiment and, although the details thereof are not therefore reiterated for the sake of brevity, when the second mode is set with the shift mechanism 9 having been electrically powered on, the movable shaft 9a retracts as shown in FIG. 26, allowing the movable electrode 7A, installed on the movable shaft 9a through the electrode fixing member 8A, to move away from the lower stationary electrode 5A and also allowing the movable electrode 7A to be held in contact with the upper stationary electrode 5B.

Figure 27:
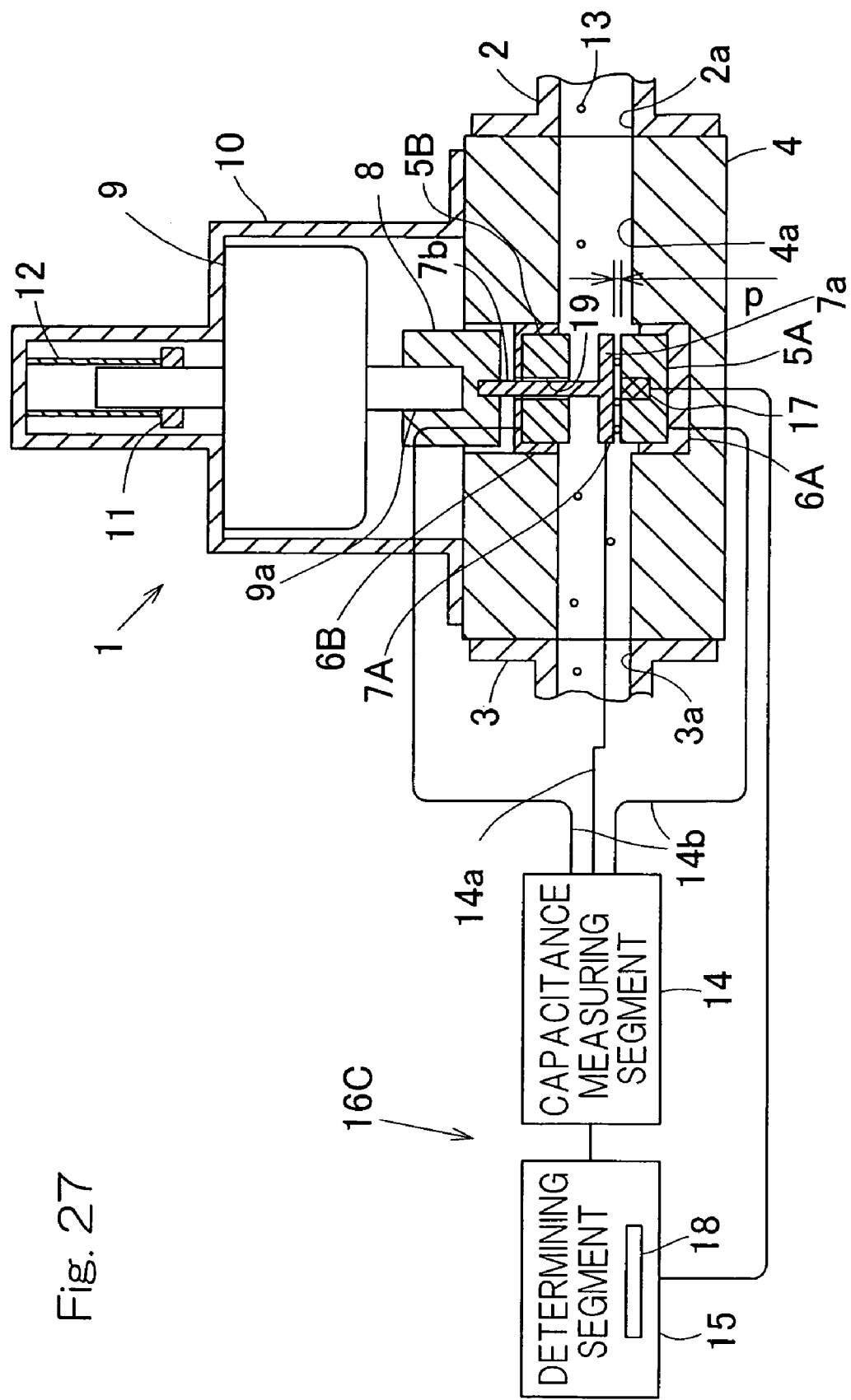
FIG. 27 is an explanatory diagram showing the detecting operation performed by the broken piece detecting sensor assembly according to the eleventh preferred embodiment operating under the second mode.

During the operation to detect the broken piece from the lubricant oil, if the lubricant oil flowing through the oil flow path 4a contains the broken piece 13 resulting form frictional wear and/or breakage of the combustion engine, the gear box and/or the bearing assemblies, such broken piece 13 flows through between the movable electrode 7A and the lower stationary electrode 5A. When the supply of the electric power to the shift mechanism 9 is interrupted under this condition, the movable electrode 7A advances towards the lower stationary electrode 5A together with the movable shaft 9a by the effect of the resilient restoring force of the compression spring 12 with the broken piece 13 consequently sandwiched between the movable electrode 7A and the lower stationary electrode 5A as shown in FIG. 27. Accordingly, the gap d corresponding to the thickness of the broken piece 13 is formed between the movable electrode 7A and the stationary electrode 5A. This gap d is then measured by the displacement sensor 17. At the same time, the capacitance C is formed between those two electrodes 5A and 7A by the presence of the gap d.

In the above described broken piece detecting operation performed by the broken piece detecting sensor assembly according to the eleventh embodiment, when the flat plates 5 and 7 referred to in the description concerning the broken piece detecting operation performed by the broken piece detecting sensor assembly according to the eighth embodiment are read as the electrodes 5A and 7A, respectively, the equations (3), (5) and (6) referred to in connection with the eighth embodiment can be equally applied in this eleventh embodiment and, hence, by measuring the capacitance C between those two electrodes 5A and 7A with the capacitance measuring 14, the value of the gap d between the electrodes 5A and 7A can be detected in a manner different from the measurement with the displacement sensor 17, the size of and the amount of the broken piece 13 accumulated can also be estimated with the value of the gap d and, therefore, it is possible to determine whether the broken piece 13 detected is electroconductive or non-electroconductive. The conduction or non-conduction determining segment 18 of the determining segment 15 has a function of determining whether the broken piece 13 detected is made up of the broken remains of electroconductive material or non-electroconductive material.

Figure 28:
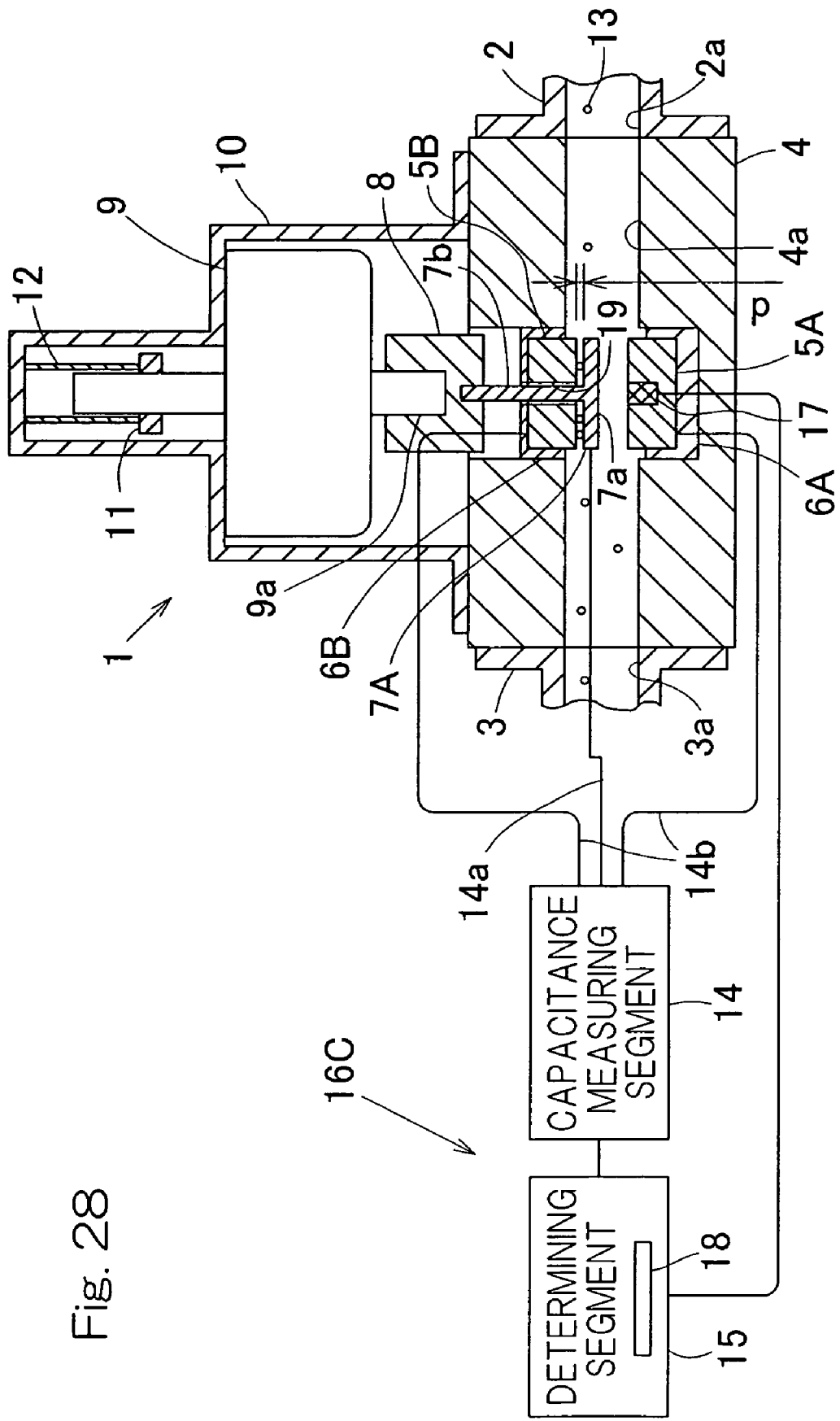
FIG. 28 is another explanatory diagram showing the detecting operation performed by the broken piece detecting sensor assembly according to the eleventh preferred embodiment operating under the second mode.

When starting from the condition shown in FIG. 27, the second mode is set with the shift mechanism 9 having been electrically powered on, the movable shaft 8a retracts further from the position assumed during the first mode as shown in FIG. 28, with the broken piece 13 sandwiched consequently between the movable electrode 7A and the upper stationary electrode 5B. Accordingly, the gap corresponding to the thickness of the broken piece 13 is formed between the movable electrode 7A and the upper stationary electrode 5B. The displacement sensor 17 then measures this gap d. In such case, the displacement sensor 17 measures the gap between the movable electrode 7A and the upper stationary electrode 5B indirectly based on the measured value of the gap between the lower stationary electrode 5A and the movable electrode 7A. At the same time, the capacitance C is formed between those two electrodes 5B and 7A by the presence of the gap d. Even in this instance, the presence or absence of the broken piece 13, the size of the broken piece 13 or the amount of the broken piece 13 accumulated can be detected and, also, determination of whether the broken piece 13 detected is made up of electroconductive material or non-electroconductive material can be accomplished, in a manner similar to that achieved when the broken piece 13 is sandwiched between the movable electrode 7A and the lower stationary electrode 5A.

Figure 29:
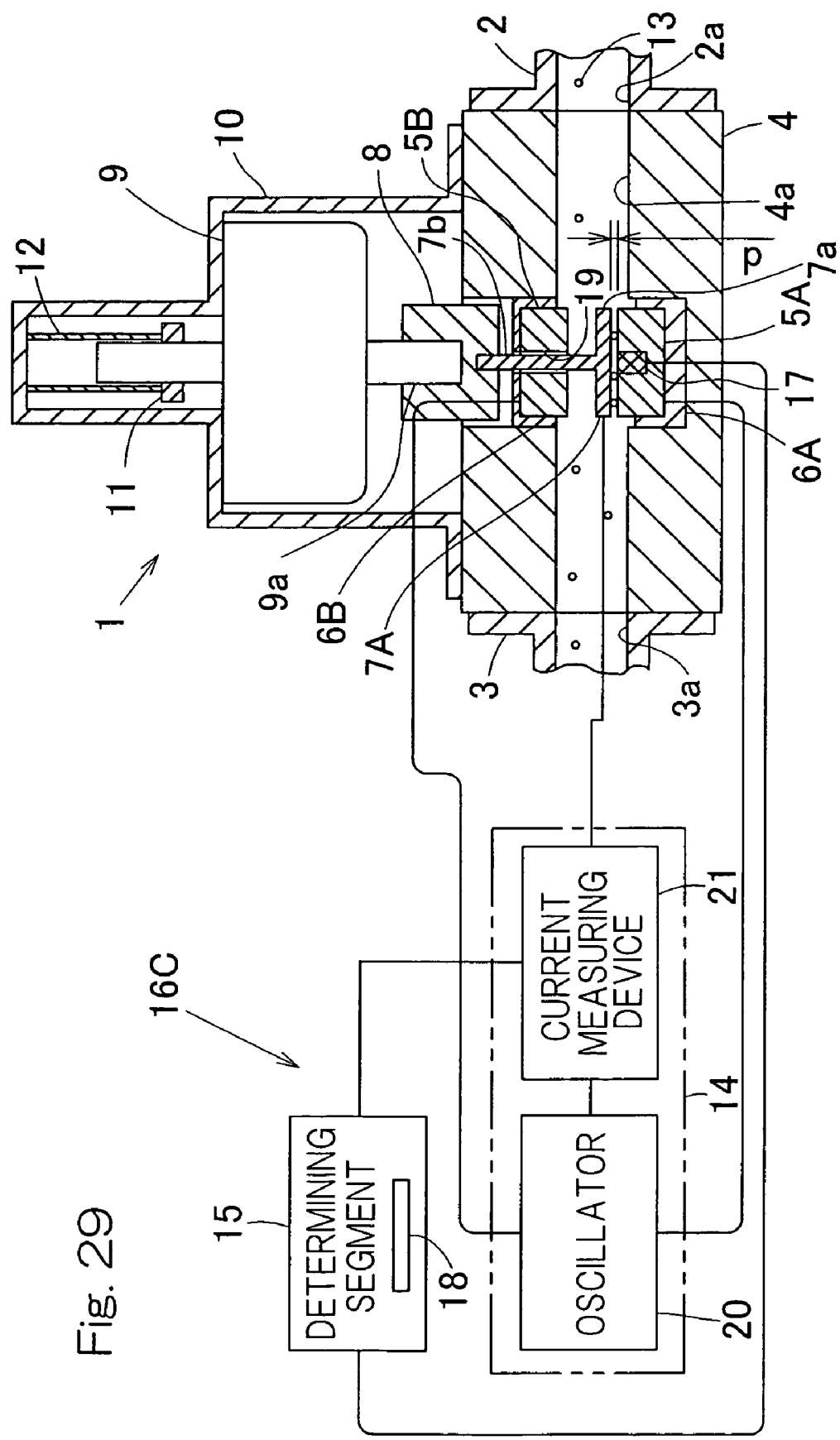
FIG. 29 is an explanatory diagram showing the detecting operation which takes place when a constructional example of a capacitance measuring segment is utilized in the broken piece detecting sensor assembly according to the eleventh preferred embodiment.

FIG. 29 illustrates an example of the structure of the capacitance measuring segment 14 which forms a part of the measuring and determining section 16C employed in the broken piece detecting sensor assembly shown in and described with reference to FIG. 24. This capacitance measuring segment 14 includes a series connected circuit of an oscillator 20 and a current measuring device 21 and is so designed and so configured that the oscillator 20 may supply an alternating current to the movable electrode 7A and the stationary electrodes 5A and 5B and the current measuring device 21 may measure the capacitance C between the electrodes 5A and 7A and between the electrodes 5B and 7A in terms of the impedance. In this case, the capacitance C can be determined from the impedance so measured by the current measuring device 21. Other structural features than those described above are similar to those shown in and described with reference to FIG. 24.

The capacitance measuring segment 14, which forms a part of the measuring and determining section 16C employed n the broken piece detecting sensor assembly shown in and described with reference to FIG. 24, may not be always limited to that having a circuit configuration shown in FIG. 29, but may have the circuit configuration shown in and described with reference to any one of FIGS. 5 and 6.

Even when the circuit configuration shown in and described with reference to FIG. 6 is employed for the capacitance measuring segment 14, the to-be-measured capacitance Ct (See the equation (2).) can be estimated in a manner similar to that shown and described in connection with the previously described third embodiment. Here, by replacing the to-be-measured capacitance Ct referred to above with the capacitance C between the electrodes 5A and 7A and between the electrodes 5B and 7A, the capacitance C thereof can be estimated.

As hereinabove described, the broken piece detecting sensor assembly according to the eleventh embodiment of the present invention is so designed and so configured that the broken piece 13 can sandwiched between the two electrodes (either between the lower stationary electrode 5A and the movable electrode 7A or between the upper stationary electrode 5B and the movable electrode 7A) with at least one of the electrodes (i.e., the movable electrode) 7A driven by the shift mechanism 9 and the gap between the two electrodes then sandwiching the broken piece can be subsequently measured by the measuring and determining section 16C to eventually detect the presence or absence of the broken piece 13, the size of the broken piece 13 or the amount of the broken piece 13 accumulated. Accordingly, the probability of the broken piece 13 being sandwiched between two of the electrodes is high and the presence or absence of the broken piece 13, the size of the broken piece 13 or the amount of the broken piece 13 accumulated can be stably detected without being adversely affected by the amount of the broken piece 13 being admixed.

Also, since in this eleventh embodiment of the present invention, of the three electrodes 5A, 5B and 7A, the gap measuring device (i.e., the displacement sensor 17 and the capacitance measuring segment 14) for measuring the respective gap is provided between the upper two electrodes (i.e., the stationary electrode 5B and the movable electrode 7) and between the lower two electrodes (i.e., the movable electrode 7A and the stationary electrode 5A) and the shift mechanism 9 is so designed and so configured as to reciprocatingly move the intermediate electrode (i.e., the movable electrode) 7A up and down so that the broken piece 13 can be sandwiched between the upper two electrodes 5B and 7A and between the lower two electrodes 7A and 5A, respective detecting operations can be accomplished at opposite ends of the single stroke of movement of the intermediate electrode (i.e., the movable electrode) 7A and, therefore, the efficiency of the detecting operation can also be increased.

Also, since in this eleventh embodiment the shift mechanism (a direct acting actuator) 9 for driving the intermediate electrode (the movable electrode) 7A is disposed outside a flow passage (the oil flow path) 4a through which a fluid (i.e., the lubricant oil) to be examined flows and is used to drive the movable electrode 7A through the insert body 7b extending through the hole 19 defined in one of the two stationary electrodes 5A and 5B, that is, the stationary electrode 5B, the three electrodes 5A, 5B and 7A can be arranged compactly.

In addition, since in this eleventh embodiment, the capacitances between the stationary electrode 5A and the movable electrode 7A and between the static electrode 5B and the movable electrode 7A are measured by the capacitance measuring segment 14, the gaps between the stationary electrode 5A and the movable electrode 7A and between the static electrode 5B and the movable electrode 7A are measured by the displacement sensor 17 and the conduction or non-conduction determining segment 18 is employed to determine from the respective outputs of the sensors 14 and 17 whether the broken piece 13 is made up of broken remains of electroconductive material or of non-electroconductive material, it is possible to determine whether the broken piece 13 detected is made up of broken remains of electroconductive material such as, for example, metallic material or non-electroconductive material such as, for example, resin or ceramics.

It is to be noted that the measuring the gap between the two electrodes 5 and 7A may not be always conducted by the combined use of the capacitance measuring segment 14 and the displacement sensor 17 such as shown and described in connection with the eleventh embodiment, but may be conducted only by the capacitance measuring segment 14 or, alternatively, only the displacement sensor 17 may be employed therefor. Also, where only the capacitance measuring segment 14 is employed, and where a coating layer made of an insulating material is provided on a surface of at least one of those two electrode, which confronts the electrode, those two electrodes will not be short-circuited with each other, even where the broken piece 13 to be sandwiched between those two electrodes is made up of broken remains of electroconductive material, and, accordingly, the capacitance between those two electrodes can be accurately measured regardless of whether the broken piece 13 is made up of the broken remains of electroconductive material or non-electroconductive material and, therefore, the presence or absence of the broken piece 13, the size of the broken piece 13 or the amount of the broken piece 13 accumulated can be detected accurately.

Figure 30:
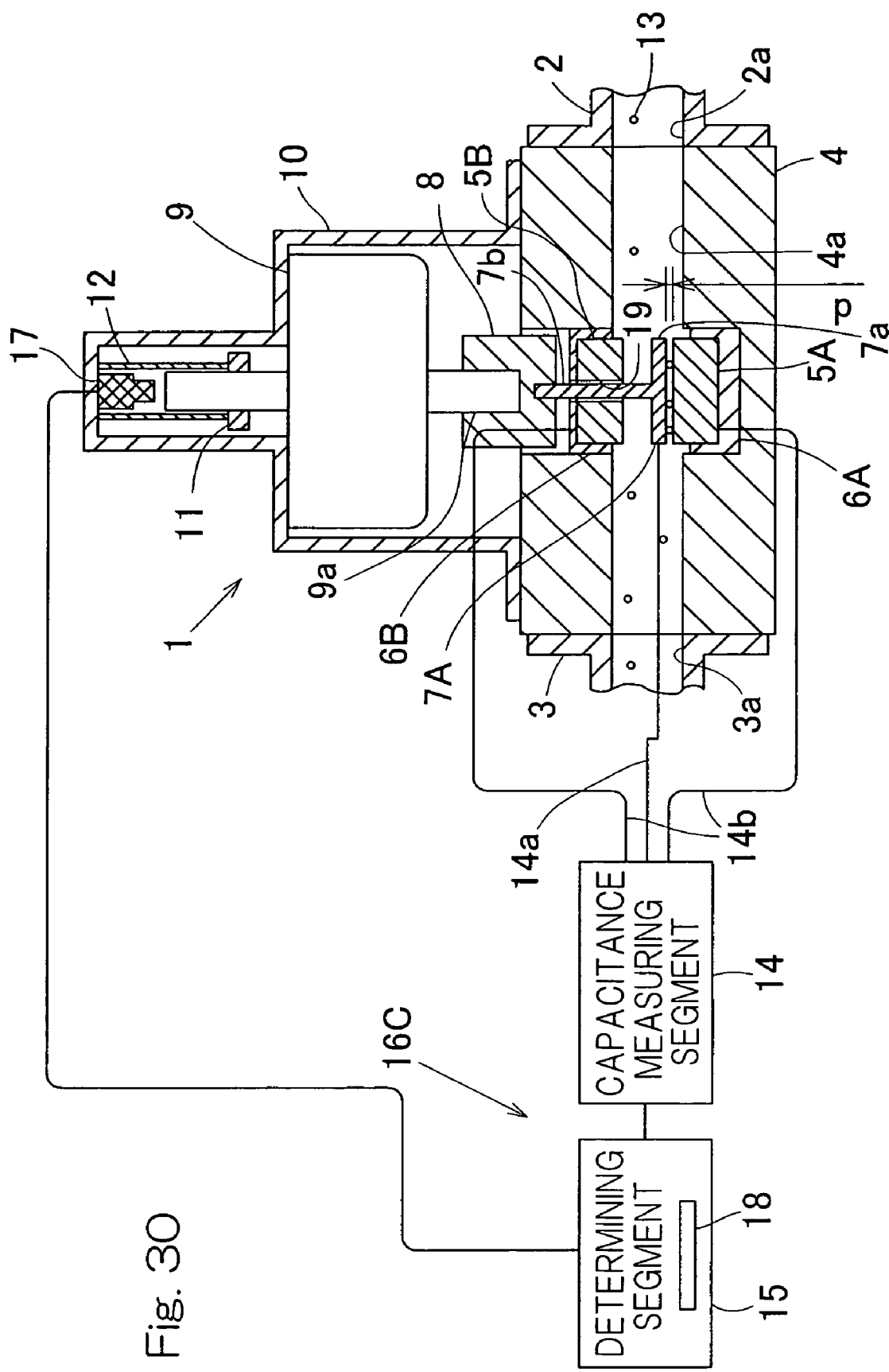
FIG. 30 is an explanatory diagram showing the detecting operation performed by the broken piece detecting sensor assembly according to a twelfth preferred embodiment of the present invention.

FIG. 30 illustrates a twelfth preferred embodiment of the present invention. This twelfth embodiment is similar to the eleventh embodiment shown in and described with reference to FIG. 24, but differs therefrom in that the displacement sensor 17 employed in the practice of the eleventh embodiment is disposed at a position confronting the rear end of the movable shaft 9a within the actuator fixing member 10.

In the case of this twelfth embodiment, the displacement sensor 17 serves to measure the amount of displacement of the movable shaft 9a, but since the movable electrode 7A is coupled with the movable shaft 9a through the fixing member 8, the gap d between the stationary electrode 5A and the movable electrode 7A and the gap d between the stationary electrode 5B and the movable electrode 7A can be detected from the amount of displacement of the movable shaft 9a.

Figure 31:
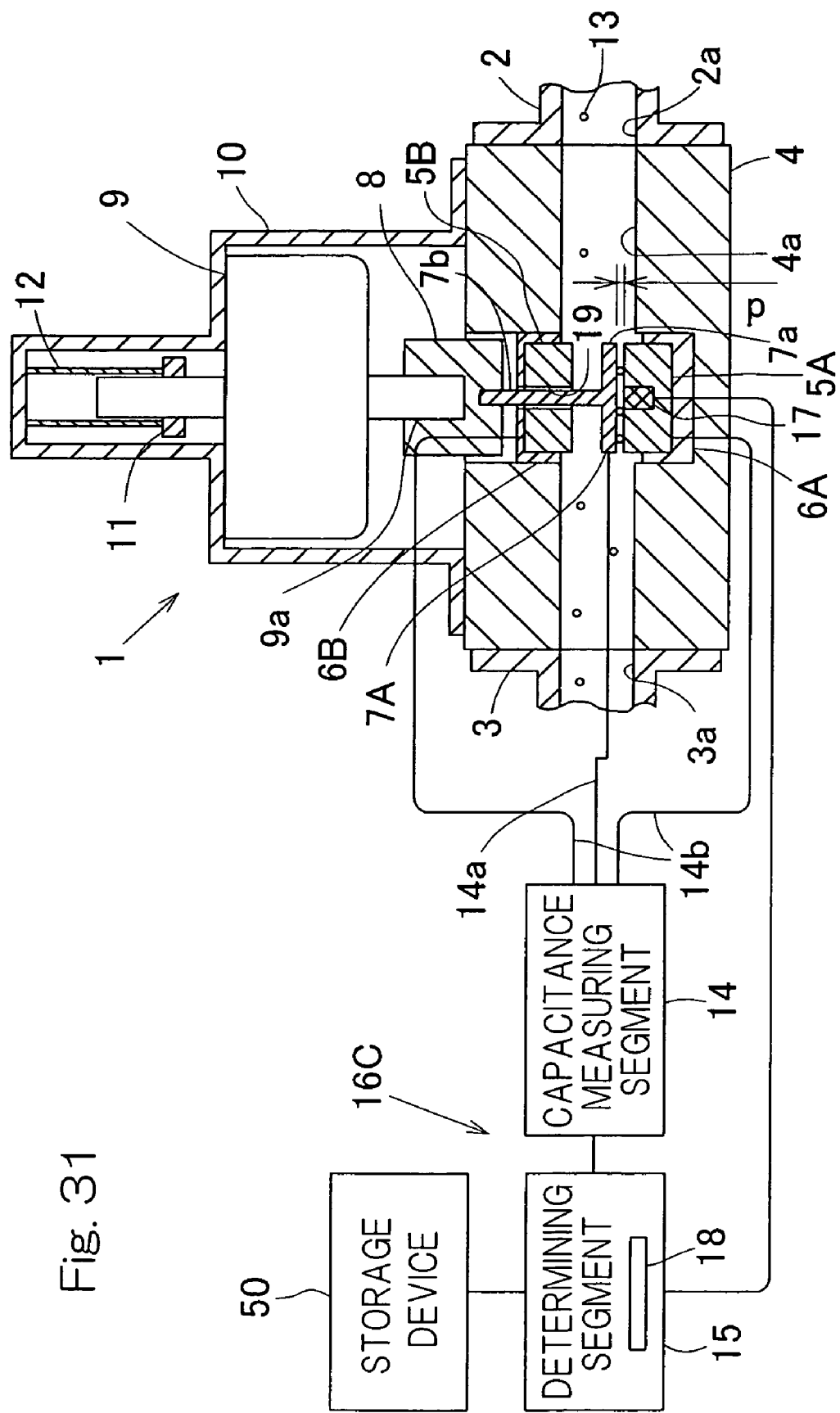
FIG. 31 is an explanatory diagram showing the detecting operation performed by the broken piece detecting sensor assembly according to a thirteenth preferred embodiment of the present invention.

FIG. 31 illustrates a thirteenth preferred embodiment of the present invention. In this thirteenth embodiment is similar to the eleventh embodiment shown in and described with reference to FIG. 24, but differs therefrom in that a storage device 50 is added to the stage next to the determining segment 15 so that the status of the broken piece 13 admixed in the lubricant oil can be monitored in real time. In this embodiment, the status of the lubricant oil can be inferred from the history of change of numerical values recorded and information on, for example, the tendency of increase of dirt and/or broken piece can be outputted. The capacitance measuring segment 14 may be of a circuit configuration shown in and described with any one of FIGS. 5, 6 and 29.

Other preferred embodiments of the present invention hereinabove fully discussed can be summarized as follows.

The broken piece detecting sensor assembly, which forms the basic structure of the present invention, is a sensor assembly for detecting broken piece admixed in a fluid and including two opposed flat plates, a shift mechanism for driving one of those flat plates towards the other of the flat plates to sandwich broken piece between those two flat plates, and a measuring and determining section for measuring a distance between those two flat plates to thereby detect the presence or absence of the broken piece, the size of the broken piece or the amount of the broken piece accumulated.

[First Mode]

The broken piece detecting sensor encompassed by this first mode of embodiment of the present invention is the broken piece detecting sensor assembly, which forms the basic structure referred to above, in which a direct current actuator is employed for the shift mechanism. The use of the direct acting actuator unlike the actuator employing a rotary drive source, no mechanism for translating a rotary motion into a rectilinear motion is required and, accordingly, the broken piece detecting sensor assembly can be assembled compact in structure. Where the direct acting actuator is employed for the shifting mechanism, unlike the actuator employing a rotary drive source, no mechanism for translating a rotary motion into a rectilinear motion is required and, accordingly, the broken piece detecting sensor assembly can be assembled compact in structure.

[Second Mode]

The direct acting actuator referred to above is of an electromagnetically operated type, a hydraulically operated type or a pneumatically operated type.

[Third Mode]

The displacement sensor forming the device for measuring the distance between the two flat plates referred to above is employed in the form of at least one or more of a magnetic type, an eddy current type and an optical type. If the displacement sensor is of the magnetic, eddy current or optical type, it is possible to detect with a simplified structure and with high accuracy.

[Fourth Mode]

The flat plate on a movable side may be elastically fixedly supported with an elastic member sandwiched between the flat plate on the movable side and the support member for supporting this flat plate. When the elastic member is so sandwiched, the flat plate can retract resiliently and such flat plate can be caused to contact the broken piece in a further stabilized attitude.

[Fifth Mode]

The flat plate on a stationary side may be fixed to a housing through an elastic member. When the flat plate on the movable side is supported by a flexible support member and, at the same time, the flat plate on the stationary side is similarly supported through the elastic member, the flat plate can retract resiliently and such flat plate can be caused to contact the broken piece in a further stabilized attitude.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

What is claimed is:

1. A broken piece detecting sensor assembly for detecting a broken piece admixed in a fluid, which assembly comprises:
   two flat plates confronting each other;
   a shift mechanism for moving at least one of the two flat plates in a confronting direction to sandwich the broken piece therebetween;
   a measuring and determining section for measuring a distance between the two flat plates to thereby detect a presence of the broken piece, a size of the broken piece or an amount of the broken pieces accumulated.

2. The broken piece detecting sensor assembly as claimed in claim 1, wherein the measuring and determining section is operable to measure the distance between the flat plates in terms of capacitance.

3. The broken piece detecting sensor assembly as claimed in claim 2, wherein the measuring and determining section estimates the capacitance by applying an alternating current and measuring an impedance.

4. The broken piece detecting sensor assembly as claimed in claim 2, wherein the measuring and determining section includes an oscillator for converting a change of the capacitance into a change of frequency and a frequency dependent capacitance estimator for estimating the capacitance from the frequency oscillated by the oscillator.

5. The broken piece detecting sensor assembly as claimed in claim 2, wherein the measuring and determining section includes a charging and discharging device for repetitively inducing charge and discharge between the flat plates and a charge and discharge time dependent capacitance estimator for estimating the capacitance from a charge and discharge time during a transient phenomenon in repetition of charge and discharge.

6. The broken piece detecting sensor assembly as claimed in claim 1, wherein the measuring and determining section for measuring the distance between the two flat plates include a displacement sensor.

7. The broken piece detecting sensor assembly as claimed in claim 1, further including an insulating layer provided in at least one of the flat plates.

8. The broken piece detecting sensor assembly as claimed in claim 1, wherein at least one of the flat plates is supported by a support member having a flexibility sufficient to permit such one of the flat plates to tilt.

9. The broken piece detecting sensor assembly as claimed in claim 8, wherein the support member supporting one of the flat plates that is movable has a coupling member capable of providing a freedom in a direction of tilting of such one of the flat plates.

10. The broken piece detecting sensor assembly as claimed in claim 1 further including an additional flat plate in the form of an electrode, wherein each of the two flat plates is employed in the form of an electrode, and wherein the shift mechanism moves at least one of these three electrodes to sandwich the broken piece between the electrode that is moved and any one of the rest of the electrodes, and the measuring and determining section measures the size of a gap, defined as a distance between the two electrodes, sandwiching the broken piece therebetween.

11. The broken piece detecting sensor assembly as claimed in claim 10, wherein those three electrodes are arranged one above the other in a vertical direction, a gap measuring device for measuring respective gaps between upper two of those electrodes and between lower two of those electrodes is provided, and the shifting mechanism is operable to move one of the electrodes, positioned intermediate between the other two electrodes, up and down to sandwich the broken piece between the upper two electrodes and between the lower two electrodes.

12. The broken piece detecting sensor assembly as claimed in claim 10, wherein the shift mechanism for moving such one of the electrodes positioned intermediate between the other two electrodes is disposed outside a fluid passage through which the fluid flows, and moves such one of the electrodes, positioned intermediate between the other two electrodes, through an insert body extending through a hole defined in one of the two electrodes provided in the form of stationary members.

* * * * *